(12) United States Patent
Kartci et al.

(10) Patent No.: US 12,007,374 B2
(45) Date of Patent: Jun. 11, 2024

(54) INTERNET OF FLORA THINGS (IoFT)

(71) Applicant: KING ABDULLAH UNIVERSITY OF SCIENCE AND TECHNOLOGY, Thuwal (SA)

(72) Inventors: Aslihan Kartci, Thuwal (SA); Quang Thang Nguyen, Thuwal (SA); Khaled Nabil Salama, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 80 days.

(21) Appl. No.: 17/925,128

(22) PCT Filed: Jul. 22, 2020

(86) PCT No.: PCT/IB2020/056920
§ 371 (c)(1),
(2) Date: Nov. 14, 2022

(87) PCT Pub. No.: WO2021/229284
PCT Pub. Date: Nov. 18, 2021

(65) Prior Publication Data
US 2023/0184733 A1    Jun. 15, 2023

Related U.S. Application Data

(60) Provisional application No. 63/025,442, filed on May 15, 2020.

(51) Int. Cl.
*G01N 33/00* (2006.01)
*H04L 67/12* (2022.01)
(Continued)

(52) U.S. Cl.
CPC ......... *G01N 33/0098* (2013.01); *H04L 67/12* (2013.01); *A01G 25/167* (2013.01); *G08B 21/18* (2013.01)

(58) Field of Classification Search
CPC .. G01N 33/0098; H04L 67/12; A01G 25/167; G08B 21/18
See application file for complete search history.

(56) References Cited

U.S. PATENT DOCUMENTS 8,836,504 B2 * 9/2014 Kohler ................ A01G 7/00
340/500
10,028,452 B2 * 7/2018 Workman ........... H04L 67/55
(Continued)

FOREIGN PATENT DOCUMENTS

EP    2359678 A1    8/2011
GB    2541468 A     2/2017

OTHER PUBLICATIONS

Chatterjee, S.K., et al., "Forward and Inverse Modelling Approaches for Prediction of Light Stimulus from Electrophysiological Response in Plants," Measurement, Jul. 2014, vol. 53, pp. 101-116, Elsevier.
(Continued)

*Primary Examiner* — Mohamed Barakat
(74) *Attorney, Agent, or Firm* — PATENT PORTFOLIO BUILDERS PLLC

(57) ABSTRACT

A system for collecting information through a plant includes a first remote detecting device attached to a first portion of the plant and configured to transmit a given signal directly through the plant; the plant, which constitutes a communication channel; a second remote detecting device attached to a second portion of the plant, which is different from the first portion, and configured to receive a signal indicative of the transmitted given signal; and a sink node that communicates with the second remote detecting device.

20 Claims, 23 Drawing Sheets

(51) Int. Cl.
    *A01G 25/16* (2006.01)
    *G08B 21/18* (2006.01)

(56) References Cited

U.S. PATENT DOCUMENTS

| | | | |
|---|---|---|---|
| 2009/0231102 A1* | 9/2009 | Hyde | H04Q 9/00 340/10.1 |
| 2018/0267006 A1* | 9/2018 | Wallbridge | G01N 33/0098 |
| 2019/0059202 A1* | 2/2019 | Lorek | A01B 79/005 |
| 2020/0236877 A1* | 7/2020 | Fujiyama | A01G 27/003 |
| 2020/0275618 A1* | 9/2020 | Akhtman | A01M 21/043 |

OTHER PUBLICATIONS

Grams, T.E.E., et al., "Heat-Induced Electrical Signals Affect Cytoplasmic and Apoplastic pH as well as Photosynthesis During Propagation Through the Maize Leaf," Plant, Cell and Environment, Apr. 2009, vol. 32, No. 4, pp. 319-326, Blackwell Publishing Ltd.

Lee, K., et al., "In-situ Synthesis of Carbon Nanotube-Graphite Electronic Devices and Their Integrations onto Surfaces of Live Plants and Insects," Nano Letters, Apr. 17, 2014, vol. 14, pp. 2647-2654, American Chemical Society.

Lew, T.T.S., et al., "The Emergence of Plant Nanobionics and Living Plants as Technology," Advanced Materials Technologies, Mar. 2020 (first published Nov. 8, 2019), vol. 5, Issue 3, pp. 1900657 1-12, Wiley-VCH Verlag GmbH & Co.

Savatin, D.V., et al., "Wounding in the Plant Tissue: the Defense of a Dangerous Passage," Frontiers in Plant Science, Sep. 16, 2014, vol. 5, Article 470, pp. 1-11.

Spoel, S.H., et al., "Making Sense of Hormone Crosstalk during Plant Immune Responses," Cell Host & Microbe, Jun. 12, 2008, vol. 3, Issue 6, pp. 348-351, Elsevier Inc.

International Search Report in corresponding/related International Application No. PCT/IB2020/056920, date of mailing Feb. 15, 2021.

Pandey, R., et al., "Integrated Electrochemical Chip-on-Plant Functional Sensor for Monitoring Gene Expression under Stress," Biosensor and Bioelectronics, Jun. 26, 2018, vol. 117, pp. 493-500, Elsevier B.V.

Written Opinion of the International Searching Authority in corresponding/related International Application No. PCT/IB2020/056920, date of mailing Feb. 15, 2021.

* cited by examiner

TABLE 1

| Sensor type | Material | Analyte | Plant | Notes |
|---|---|---|---|---|
| genetically encoded biosensors | | ROS, $Ca^{2+}$ | arabidopsis thaliana | |
| nanoparticle-based sensors | SWNT, P-SWNT | proteins, small molecules, and carbohydrates | | ultralow photobleaching, fluorescence in the transparency window of leaf tissue and high spatiotemporal resolution, suitable to monitor short-lived plant signaling molecules |
| viva optical sensor | DNA-wrapped SWNT | nitric oxide | Spinach Leaf lamina | boronic acid-conjugated quantum dots |
| quantum dot probes | SWNT-based sensor | glucose | | |
| wearable sensor | | water content | tomato plants | leaf thickness correlated it with the plant water content |
| printed conformal conjugated polymer electrode | | cellular water content | | perform bioimpedance spectroscopy and detect tissue damage caused by dehydration and ultraviolet exposure |
| wearable gas sensor | graphene-based nanomaterials | relative water humidity | leaf surface | intensity and wavelength of incident light, carbon dioxide, air humidity, and temperature effects. These measurements are routinely done with gas exchange chambers |

FIG. 2A

TABLE 1 CONTINUED

| Sensor type | Material | Analyte | Plant | Notes |
|---|---|---|---|---|
| | mixture of graphite and polypyrrole-functionalized SWNT ink | amino groups in DMMP | lucky bamboo surface | |
| | mixture of carbon nanotubes and copper(I) | ethylene | various fruits | initiates the ripening of fruit, promotes seed germination and flowering, and responsible for the senescence of leaves and flowers |
| stomata sensor | | photophosphorylation, proton pumps ($K^+$, $Cl^-$, $NO_3^-$, and $malate^{2-}$) | | to demonstrate its dynamics depends on light color and intensity |
| light emission | luciferase protein and luciferin substrate | ATP molecule, $O_2$, $Mg^{2+}$ ions | photinus pyralis | |
| biofuel | glassy carbon electrode coated with glucose oxidase and bilirubin oxidase enzymes | glucose | cactus | biofuel cells operating in planta, with biocompatibility and enzyme efficiency remain as the major bottlenecks |
| coating $Co_3O_4$ to 3D graphene electrodes | | glucose oxidation, oxygen reduction | biofuel cells | |
| Textile-based OECT | PEDOT:PSS | sap electrolyte concentration | tomato plant | to monitor, in vivo and in real time, variations in the solute content of the plant sap |

FIG. 2B

INTERNET OF FLORA THINGS (IoFT)

CROSS-REFERENCE TO RELATED APPLICATIONS

This application is a U.S. National Stage Application of International Application No. PCT/IB2020/056920, filed on Jul. 22, 2020, which claims priority to U.S. Provisional Patent Application No. 63/025,442, filed on May 15, 2020, entitled "INTERNET OF FLORA THINGS (IoFT): FROM INTRA-PLANT SENSOR NETWORKS TO COMMUNICATION SYSTEMS (FLORA-FI)," the disclosures of which are incorporated herein by reference in their entirety.

BACKGROUND

Technical Field

Embodiments of the subject matter disclosed herein generally relate to a system and method for exchanging information along communication channels partially routed through one or more plants, and more particularly, to a communication system that partially uses plant communication channels for monitoring the health of the plants and/or characteristics of the ambient air and/or soil.

Discussion of the Background

Plants represent a unique biological system which can self-repair, grow autonomously, and fix carbon dioxide through photosynthesis. They are also in constant fluidic exchange with their surroundings and are very sensitive to changes in the external environmental conditions due to their nature. By interfacing plants with functional nanomaterials, or biocompatible electronic materials, the rich flow of information that plants exchange with their surroundings can be accessed in real time, enabling the creation of plant-based sensors. Moreover, the plant internal signaling pathways, indicative of the plant stress levels, can also be monitored as a proxy for crop health status for agricultural applications and then, this information, together with real-time surrounding information can be conveyed to remote electronic systems for environmental monitoring.

A typical plant structure and functions are illustrated in FIG. 1, from an engineering perspective. More specifically, the typical plant 100 includes a root system 110, which is a vast network used for water extraction and nutrients from the soil. A stem 111 is connected to the root system 110 and the stem branches into smaller stems 112, which together form a conductive network for transporting water and minerals between the roots and the shoots. The stem 115 includes xylem 112A and phloem 112B. Plural leaves 114 are attached to the stem 111 and each of them includes a stomata 115, which regulates the exchange of carbon dioxide, oxygen, and water vapor with the ambient. The transpiration enables the transport of water and nutrients from the roots to each leaf via capillary action.

The leaves 114 also include a plant cell 116, which is made of (1) a nucleus, which stores nuclear DNA and regulates the cell activities, (2) chloroplast, where the photosynthesis takes place, (3) mitochondrion, which produces the energy, and (4) vacuole, which is a storage area for nutrients and waste matter.

The presence of any trigger 118 (e.g., chemical, or insect, etc.) on or around a leaf makes the plant to start signaling, e.g., producing electrical and chemical signaling upon biotic and/or abiotic stress. One such mechanism involves the production of volatile organic compounds for external signaling 120 and interplant communication. While various sensors for tapping into the internal communication of a plant have been developed, there is no system that integrates plural plants and the plant intercommunication for monitoring the environment and the health of the plants.

Thus, there is a need for a new system that is capable of interacting with plural plants and using the information from these plants for agricultural and environmental purposes.

BRIEF SUMMARY OF THE INVENTION

According to an embodiment, there is a system for collecting information through a plant, and the system includes a first remote detecting device attached to a first portion of the plant and configured to transmit a given signal directly through the plant; the plant, which constitutes a communication channel; a second remote detecting device attached to a second portion of the plant, which is different from the first portion, and configured to receive a signal indicative of the transmitted given signal; and a sink node that communicates with the second remote detecting device.

According to another embodiment, there is a system for determining a health of a plant, and the system includes plural transmitters attached to various first portions of the plant and each configured to transmit a given signal directly through the plant; the plant, which constitutes plural communication channels; a receiver attached to a second portion of the plant, which is different from the first portions, and configured to receive corresponding signals indicative of the transmitted given signals; a processing device that communicates with the second remote detecting device and processes the corresponding signals to generate a health report of the plant; and a display that displays the health report of the plant.

According to another embodiment, there is a method for determining a health of a plant, and the method includes sending into the plant plural given signals from plural transmitters attached to various first portions of the plant; receiving at a receiver, attached to a second portion of the plant, which is different from the first portions, corresponding signals indicative of the transmitted given signals; transferring to a processing device, which communicates with the second remote detecting device, the corresponding signals; processing at the processing device the corresponding signals to generate a health report of the plant; and displaying on a display the health report of the plant.

BRIEF DESCRIPTION OF THE DRAWINGS

For a more complete understanding of the present invention, reference is now made to the following descriptions taken in conjunction with the accompanying drawings, in which:

FIGS. 2A and 2B present a review of the various sensors existing on the market for monitoring or detecting a parameter associated with a plant;

DETAILED DESCRIPTION OF THE INVENTION

Figure 1:
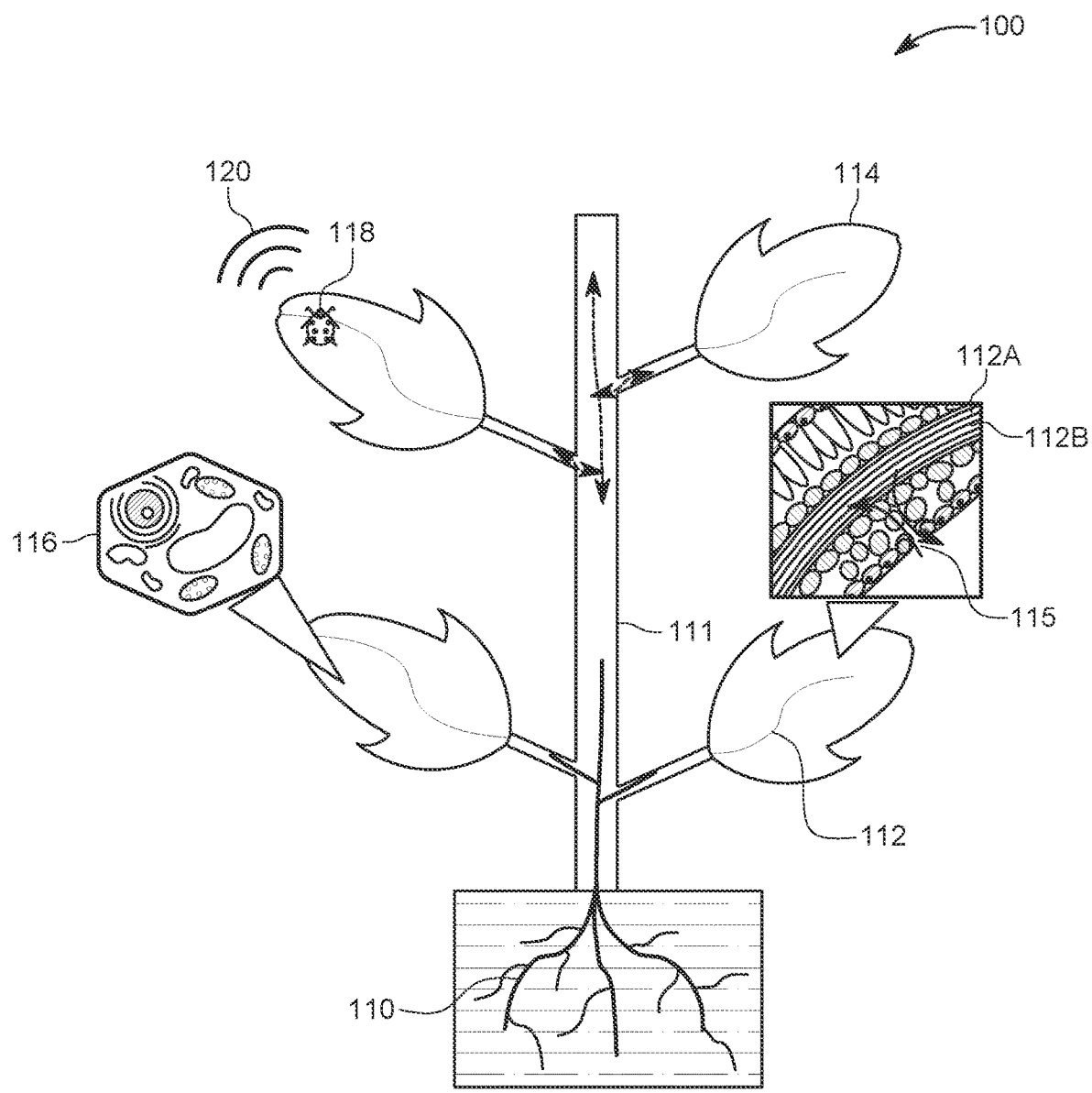
FIG. 1 is a schematic diagram of a general configuration of a plant.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to first and second remote detecting devices attached to a single plant and using the plant as a communication channel. However, the embodiments to be discussed next are not limited to two remote detecting devices, or a single plant, but may be applied to plural detecting devices distributed over plural plants.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Various organs and organelles of the plants can be potentially exploited for engineering applications ranging from environmental and biochemical sensing to energy harvesting and transport. For instance, the roots, stem, and leaves of the plants are made up of a natural circuitry consisting of vascular bundles, enabling rapid and efficient transport of water, nutrients, peptides, and ions between the roots and the shoots. The plant leaf is a complex organ made of specialized tissues such as the palisade mesophyll, spongy mesophyll, and the epidermis layer. The plant leaf cell contains chloroplasts with light-harvesting complexes, which endow plants with a unique ability to fix carbon via photosynthesis. In addition, they utilize a complex set of electrical and chemical signaling pathways, as well as volatile organic compounds (VOCs) production, for rapid intra- and intercellular communication in response to biotic and abiotic stresses [1]. As plants are abundant and widely distributed in the nature, tapping into these unique plant functions using nanotechnology and electronics constitutes a compelling proposition from an engineering perspective, for the creation of biomaterials with novel properties in environmental sensing, energy storage, conversion, harvesting applications, crop health monitoring, and field imaging.

However, to be able to tap into the intra- and intercellular communication of the plants, sensors capable of intercepting this information are necessary. It is known that in response to external changes in the environment, plants utilize rapid intercellular communication for integration of responses in different tissues and organs [2]. These signals are composed of controlled production of phytohormones accompanied by rapidly propagating electrical potential waves of cell membrane polarization [3]. Tapping into these electrical signals can provide access to the wealth of information that plants are experiencing, such as changes in temperature, light intensity, mechanical forces, gravity, air and soil pollution, drought, deficiency or surplus of nutrients, and attacks by insects or pathogens. Measuring these signals is achieved by interfacing plants with electrodes, which are placed either on the leaf surface, or through insertion into the leaf tissues.

When using a plant as a biochemical sensor, the number of analytes near the sensor is higher as the analytes are transported from the roots to leaves (assuming a much slower rate of analyte breakdown as compared to the sensor response rate). This effect represents a natural way of preconcentrating analytes, easing the detection process. Wong et al. (Wong, M. H., Giraldo, J. P., Kwak, S. Y., Koman, V. B., Sinclair, R., Lew, T. T. S., Bisker, G., Liu, P. and Strano, M. S., 2017. Nitroaromatic detection and infrared communication from wild-type plants using plant nanobionics. Nature materials, 16(2), pp. 264-272.) estimated the accumulation rate in the leaf to be 1.28 nmol min$^{-1}$ for $400\times10^{-6}$ m picric in the soil uptaken by a plant with the maximum flow rate of 1.6 mL min$^{-1}$. The reported results demonstrate the ability of the nanobionics to convert living plants into self-powered autosamplers and chemical sensors for groundwater and environmental pollutants.

Previously bulky modern sensors are becoming thinner over time, leading to the emerging area of wearable electronics, a field mainly developed from interfacing of flexible electronics with the mammalian epidermal cells. This allows wearable sensors to become transparent, so not to limit the plant's photosynthesis, flexible, to allow phototropism, and porous, to sustain effective gas exchange with the surrounding. Wearable sensors can probe outer properties of leaves and cells, such as the leaf thickness, chlorophyll content, and cell turgidity. These properties reflect biochemical processes occurring inside the cells that are, in turn, dependent on the outer conditions that plants experience.

Besides gaseous exchanges, plants also generate VOCs that act as secondary metabolites for plant communication with other organisms or with the environment [4]. Certain VOCs are produced when plants are subjected to very specific threats, such as pest attack or abiotic stress. Patterned directly onto the leaf surface, wearable sensors can tap into this valuable information that plants collect and process.

Moreover, from the energy standpoint, plants represent autonomous systems that harvest energy from water, sunlight, and carbon dioxide with self-repair capabilities. They are also widely distributed in nature, motivating their application as an alternative energy source especially for distributed and remote autonomous devices. Even though there are some studies that note the energy consumption during photosynthesis, the stored amount of energy might be used to drive multiple applications. The chemicals required for light emission reaction, namely luciferin, luciferase, and coenzyme A, were encapsulated in biocompatible poly (lactic-co-glycolic acid) (PLGA), silica, and chitosan nanoparticles. Introduction of these nanoparticles to other parts of the plants such as the stem and via the root uptake will also help achieve a more uniform distribution of nanoparticles throughout the plant for potentially brighter and longer light illumination.

A plant constitutes a network of cells that each produces glucose via the photosynthetic route. Glucose acts as a chemical liquid fuel that can release up to 3574 Ah $kg^{-1}$, which is 85-fold greater than the energy released by lithium-ion batteries (42 Ah $kg^{-1}$). To further increase the energy output to sufficiently power everyday electronics, the incorporation of nanomaterial-based electrodes in plant biofuel cells can be explored. Nanostructured materials are a promising alternative to bioenzymes due to their excellent catalytic and electrochemical properties. Commercial translation of such precision agriculture techniques has relied also on soil-implanted sensors that monitor the soil water and ionic content. However, due to the complexities in crop growing conditions, the spatial variability of water and nutrients in the soil is significant and may change between seasons.

Table 1 shown in FIGS. 2A and 2B lists the various sensors that have been developed with different techniques for different purposes with regard to the plants. In the table, ROS stands for reactive oxygen species, $Ca^{2+}$ is the intracellular calcium, SWNT stands for single-walled carbon nanotubes, P-SWNT is PVA coated SWNT, DMMP is the dimethyl methylphosponate, ATP is the adenosine triphosphate, and OECT stands for the organic electrochemical transistors. Any of these sensors can be used in the system to be discussed herein.

Figure 3:
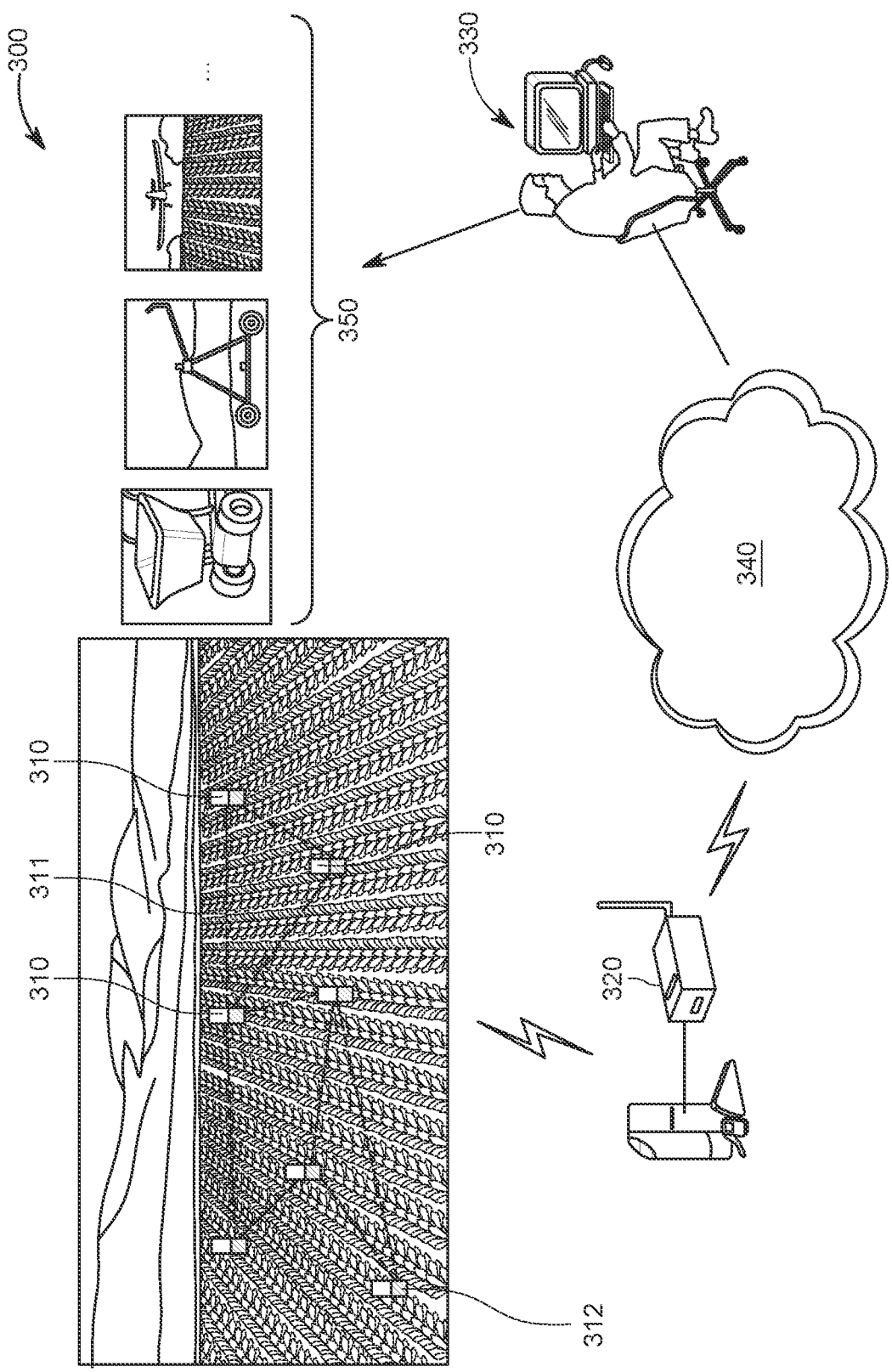
FIG. 3 illustrates a schematic diagram of a plant based network that collects information about the plant or its ambient and transmits that information along a communication channel that is partly based on the plant.

Based on any of these sensors or a combination of these sensors, an architecture for agriculture cyber physical systems may be designed to include the following parts: remote detecting devices, one or more plants, a sink node, a traditional communication network, a control center, and a farming facility. Such a system 300 is schematically illustrated in FIG. 3. The remote detecting devices 310 are placed in the agricultural system 300, i.e., on the ground, on the plants 312, or around the plants, to gather physical or environmental information. The remote detecting devices 310, which are discussed in more detail later, transmit various data among themselves, via communication paths 311 that include one or more of the plants 312, and eventually this data is sent to a sink node 320. In one embodiment, the sink node 320 may be a computing device, for example, laptop, tablet, cell phone, etc. The sink node 320 manages the information traffic between the remote detecting devices 310 and the remote control center 330 through a wired or wireless Internet network 340. The remote control center 330 hosts a processing unit that is able to store the collected data from the local sites and performs further analyses in order to make appropriate decisions concerning the evaluation of the commands that will be directed to the farming facility. Modern farming applications 350, such as fertilizing, irrigating, insecticide spraying, etc., are then automatically deployed by remote supervisory command orders from the control center 330. The remote detecting devices 310 may also be used for tracking the water status of the soil, temperature, energy bank state of the charge, and storage water level.

In one embodiment, it is possible to have sensors attached to the remote detecting devices to determine a glucose level in the plant, as the glucose is an indicator of the growth and developmental processes in the plants. Thus, the glucose is a key signaling molecule.

Various research has shown that a stoma of a plant can be viewed as a pixel for light. This concept can be extended to multiple pixels, giving rise to the concept of a camera plant, where the response and position of every pixel can be converted into the image that a plant perceives. The camera plant can potentially turn plants into natural detectors that directly capitalize on plant's innate ability to distinguish different wavelengths of the incident light. In one embodiment, an optical sensor readout can be relayed to a portable Raspberry Pi-based platform, a technology that is like a cell phone-based camera, enabling living plants to function as infrared communication devices to external electronics at remote distances. Such interfacing with the electronic system could also potentially allow the integration of the plant-based sensors with the Internet of Things (IoT), forming a distributed sensor network that can collect and transmit information about both the crop health status and the surrounding environment.

As the characteristics of the electrical signals transmitted through the plants vary with the external stresses [5], the development of nondestructive sensing tools would enable a real-time flow of specific information between the plants and the humans, thus providing the plants with novel and non-native functions, for example, to serve as self-powered communication devices and autonomous reporter about their health, as well as their surrounding environment. These electrical signals can further be used to control man-made technologies. For example, it was shown that a plant-based actuation robot system can bring a plant in the direction of light when the plant detects the presence of light. In this application, the electrical signal induced in the plant, when the plant was subjected to different light intensities, was used to move the robot system so that the plant moves to the optimal illumination location.

According to one embodiment, it is possible to integrate one or more remote detecting devices with plural plants and to collect information from the sensors associated with the remote detecting devices, by using the plants as communication channels, so that a communication network between the remote detecting devices 310 and the sink node 320 include one or more parts of one or more plants. In this way, a more affordable and proactive horticulture systems can be achieved through implantable or wearable monitoring systems capable of early detection of abnormal conditions resulting in major improvements in the quality of plants.

This goal can be achieved through a network consisting of intelligent, low-power, micro and nano-technology sensors and actuators, which can be placed on the plant, or implanted in the plant (or even in the plant's blood stream that contains nitrogen, phosphorus, and potassium), thus providing timely data. Such networks are commonly referred to as Intra-Plant Sensor Networks or Plant Area Networks (PANs).

Sensors that are suitable for such a system are based on electrochemical sensors and biosensors' that use nanomaterials. The nanoscience and nanotechnology have strongly influenced the design and construction of recent electrochemical sensors and biosensors paving the way for nanostructured electrode surfaces which are able to improve the quality of the electrochemical response and allowing the efficient immobilization of biomolecules. These sensors can also be used for detecting alive tissues in plants on their leaves, or roots. In this regard, a plant equipped with botanic sensors of this kind—called herein a cyberplant—can provide information about the moisture content, cell composition and quality of the crop itself, as well as environmental factors such as soil and air quality, wind speed, solar strength and rainfall. Therefore, fast and reliable data about the plant's condition can make it possible for plants to be watered when required and fertilized more efficiently.

Thus, in one embodiment, a wireless (radio) plant area network, PAN, is created among the plural plants, and this wireless network is used for transmitting information between the plants and the sink node. Such PAN consumes only a few microwatts and its costs is very low. Therefore, in this embodiment, the plants themselves may be used as low-cost sensors and/or as communication channels for the PAN. The PAN and the plants contribute to optimizing the input usage of micronutrients and water, both of which are high priority goals in the context of achieving agricultural sustainability and obtaining a high crop.

Monitoring the agricultural changes and environmental factors should be detected at the same time for reliable evaluation of the plant status. The circuit boards that can record and transmit information are designed and implemented together with the sensor/electrode. In one embodiment, these cyborg plants are used to detect parasites and pollutants in crops, or they could play a role in what's called precision agriculture, telling farmers when they need more water or more nutrients or less. More broadly, the plants could monitor the effects of acid rain in the environment or the health of city parks. With the intra-plant communication network discussed herein, the sensors may get their signal from any part of the plant, from the root to leaf, leaf to root through stem, etc. in a simple, low-cost and energy efficient way.

Moreover, unlike traditional chemical analysis, performed in well-equipped laboratories with the aim to identify and quantify small amounts of analytes, the PAN helps the system 300 to supply quantitative and qualitative information about a chemical process that can be used not only to monitor and control the process, but also to optimize its efficient use of energy, time, and raw materials. In addition, it is possible to simultaneously minimize plant effluent release and to improve product quality. While the effect of the electrode position relative to the plant organs of interest was studied in [6] with regard to unique plant responses to light conditions, and a mathematical model was built to describe the relationship between the light, as an environmental stimulus, and the electrical response, as the measured output for a bay leaf, there is no disclosure in this reference about using the PAN for transmitting information.

The possibility to continuously monitor the plant opens new perspectives, for example, to dissect the mechanisms that take place in the plant during abiotic stress response, to understand where and when different ions are synthesized, allocated and translocated in normal and stress conditions, and, finally, to understand the links existing among genotype, environment, and phenotype.

Figure 4:
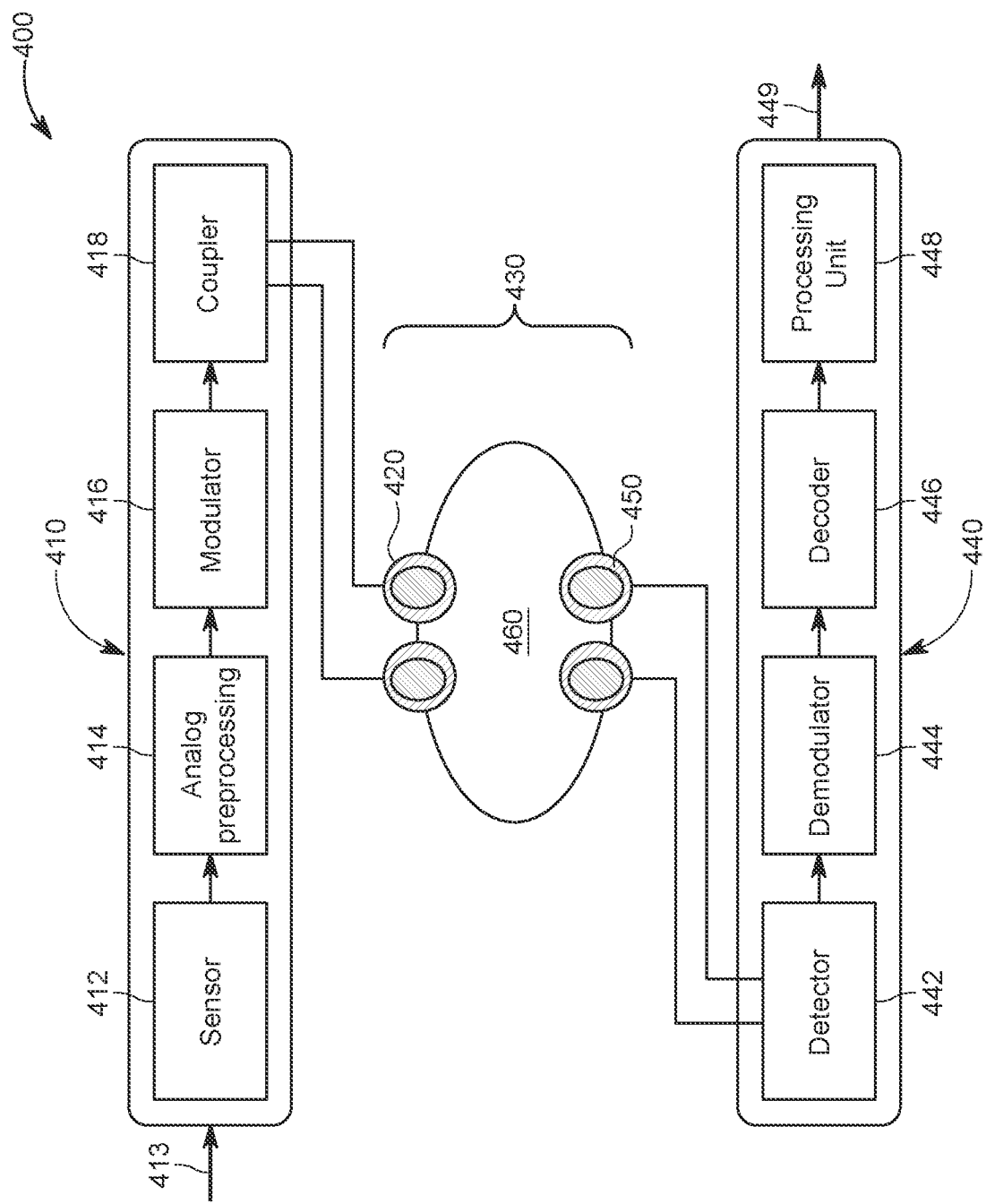
FIG. 4 illustrates in more detail the plant based network, which includes a first remote detecting device, a plant, and a second remote detecting device that communicates with the first remote device exclusively through the plant.

The PAN and associated remote detecting devices are now discussed in more detail. A portion of the PAN communication system is schematically illustrated in FIG. 4 and includes a first remote detecting device, for example, a transmitter 410, a communication channel 430, and a second remote detecting device, for example, a receiver 440. The intra-plant communication (IPC) transmitter 410 includes at least a sensor 412 that is configured to record information 413 about the plant or the environment of the plant. The transmitter 410 further includes an analog-to-digital converter (ADC) 414 for analog preprocessing and for converting the analog signal generated by the sensor 412 into a digital signal. The digital signal is provided to a modulator 416 to perform various digital processing, for example, amplification and/or correction, encoding (which is discussed later), etc., and the output signal is provided to a coupler 416, which has one or more electrodes that are configured to interact with the plant. The choice of sensors 412 depends on a desired application, i.e., sensors of physiological functions for obtaining signals in agriculture applications, or cameras and microphones for media devices.

An IPC receiver 440 may include a detector 442, which is connected to the electrodes 450, and is configured for receiving various signals from the plant 460. The detected signal is provided to a demodulator 444, for demodulating the received signal, as it was modulated at the transmitter. Next, the demodulated signal is provided to a signal decoder 446 for extracting the information encoded at the transmitter. A signal processing unit 448 further amplifies and processes the decoding information and provides to the user the information 449 corresponding to the recording signal 413. The transmitter and receiver units can be also embedded in a single IPC transceiver with a common control unit. The IPC transceiver units needs to be small and light and have full integration ability and energy efficiency and have the ability to transmit at low power. The transmitter output power should be kept as low as possible due to the health and safety reasons and battery longevity issues, yet high enough for the signal to be detected by the receiver placed at the desired distance from the transmitter. Carrier signal frequency, data rate, modulation method, and communication interface all depend on the choice of the coupling technique and application, as discussed later. The developed systems differ by the coupling method, the coupling amplitude, the chosen frequency range, the signal modulation method, and the achieved data rates.

The communication channel 430 refers to a physical transmission path between the transmitter 410 and the receiver 440 and in this application, it includes at least a part of the plant 460 and/or a surrounding environment, but also plural plants. The transmitter and receiver have corresponding electrodes 420 and 450, which are configured to be connected to the surface of the plant 460, but can also be left floating, depending on the signal frequency, coupling technique, and application.

The communication channel can include not only a part of a given plant, but any member of the fungi kingdom. For example, while mushrooms might be the most familiar part of a fungus, most of their bodies are made up of a mass of thin threads, known as a mycelium. These threads act as a kind of underground internet, linking the roots of different plants. This means that a tree in the garden is probably connected via the mycelium up to a bush or a plant or another tree, several meters away. All these elements from the plant and/or the fungi kingdom can make up the communication channel 430. Thus, although FIG. 4 shows that the communication channel 430 includes only a plant 460, in reality, the communication channel includes any combination of plants and fungi, irrespective of their number.

Scientists believe that the plants are not just sitting quietly in the garden growing in the sun. By linking to the fungal network discussed above, it is believed that the plants help out their neighbors by sharing nutrients and information—or sabotage unwelcome plants by spreading toxic chemicals through the network. For instance, there are plants that do not have chlorophyll, so unlike most plants, they cannot produce their own energy through photosynthesis. Some of these plants, such as the phantom orchid, get the carbon they need from nearby trees, via the mycelia of fungi that both are connected to. Animals might also exploit the fungal internet. Some plants produce compounds to attract friendly bacteria and fungi to their roots, but these signals can be picked up by insects and worms looking for tasty roots to eat. The movement of these signals through the fungal mycelia may inadvertently advertise the plants presence to these animals.

Further, it is known that large trees help small, younger ones using the fungal internet. Without this help, many seedlings would not survive. In one study, seedlings in the shade, which are likely to be short of food, got more carbon from the donor trees. Based on all these observations, the inventors have discovered that all these communication channels between the various parts of the plants and fungi can be harvested into an Internet of Flora Things (IoFT) and the existing sensors can be connected to this network for controlling the input to the plants, the environment, and obtaining information based on which corrective actions with regard to both the plants and the environment can be taken.

Figure 5:
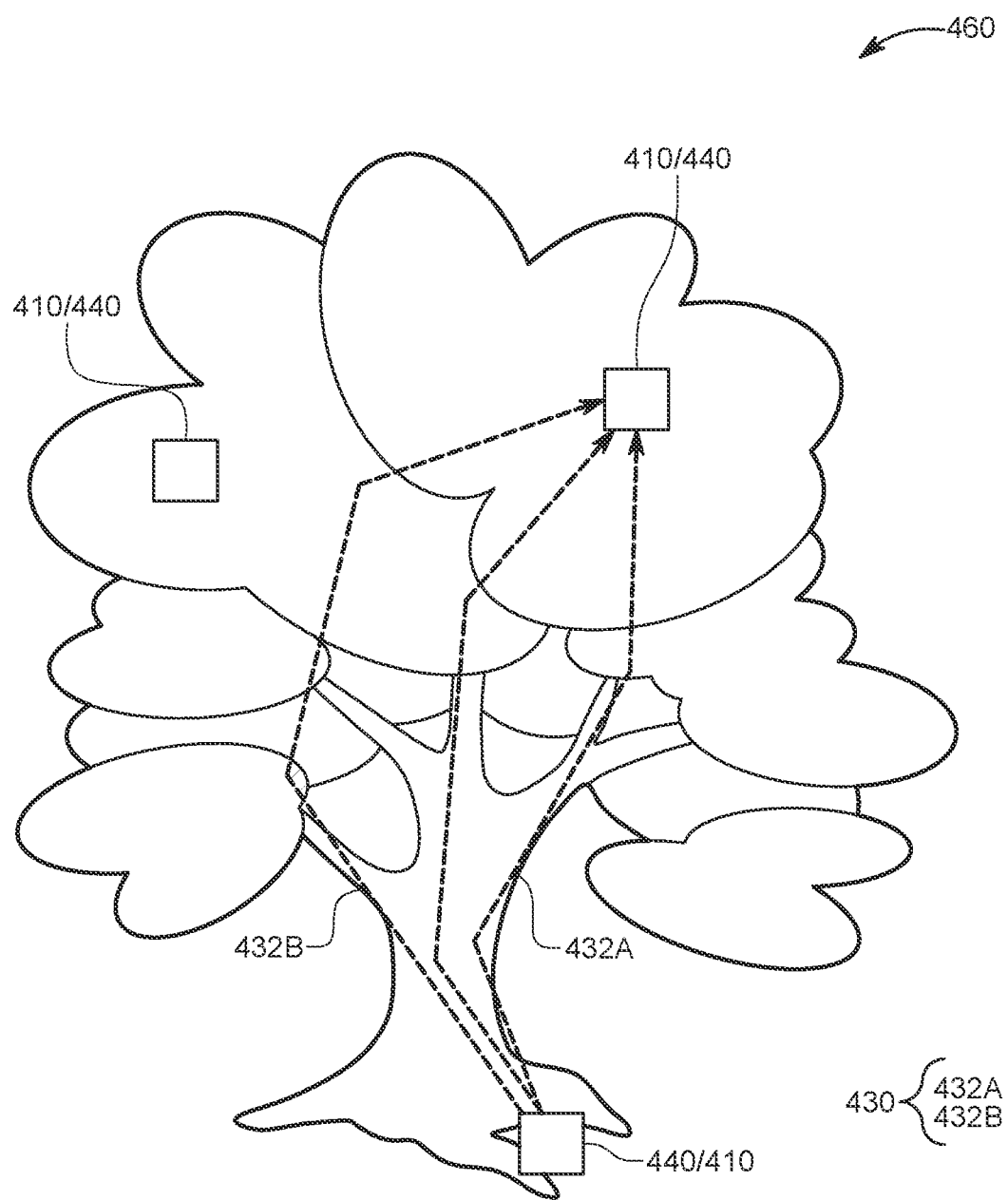
FIG. 5 illustrates a system of remote detecting devices that are distributed over the plant for generating a health report of the plant or for collecting information about the plant and/or the ambient of the plant.

The IoFT would also allow the scientists to obtain information about the plants by applying an "X-ray" or a "CT-scan" like procedure to the plants. For example, as illustrated in FIG. 5, one or more transmitters 410 may be placed around the plant (tree) 460, for example, at its extremities, while a receiver 440 may be placed on the roots or close to the roots. Then, an electrical signal is generated by the transmitter 410 and the receiver 440 receives that signal along multiple paths 432A and 432B through the plant 460, which together form the network 430. One skilled in the art would understand that the transmitters 410 may be replaced with receivers 440 and the receiver 440 may be replaced with the transmitter 410 and still this procedure works.

Then, a desired signal is applied at the transmitter 410, and a corresponding signal is recorded at the receiver 440. These applied signals may be designed to mimic various conditions experienced by the plant, for example, high concentration of $CO_2$, high temperature, etc. In this regard, the above noted parameters may be simulated around the plant, in a controlled environment, and the natural responses of the plant are recorded. Then, a classification of the different signals that the plant produces may be performed in order to determine what kind of natural stimulus has been applied to the plant. For example, it is known which electrical pattern is typically produced by a sunflower when it is suffering from drought. Then, based on this response, it is possible to look for that pattern in the sunflower plants that are hooked to the communication network 430 and listen to these plants to understand when they want water, through specific electrical signals. This means that the plants need to be interfaced with electronic devices and then connected to the PAN 430. The plant is turned into a kind of cyborg, or plant-borg. The collected information from these plants can be processed by an Artificial Neural Network (ANN) or any other algorithms.

Possible communication paths within a given plant may apply to leaf-leaf, vent-leaf, vent-vent, root-leaf, root-vent, and root-root. The inventors have used these six different mediums to simulate the signal transmission, the gain response of each medium was studied, and based on the channel gain information, an appropriate modulation technique was selected to transmit the signal. Then, a modulation technique was applied to show the transmitted and received data using different mediums of the plant. The frequency of the modulation has been chosen to be 40 MHz, which is a compromise between the data rate and the loss of the channel. Moreover, the bit error rate was calculated, and constellation figures, which shows the fairness of the modulation, were generated. In this case, the channel gain (path loss) is not as high as compared to the air (around −100 dB). If the plant channel is considered as a wire channel (as opposite to a wireless channel), there is no need to transmit the information at high frequencies. In other words, the baseband signal can be transmitted directly.

Figure 6A:
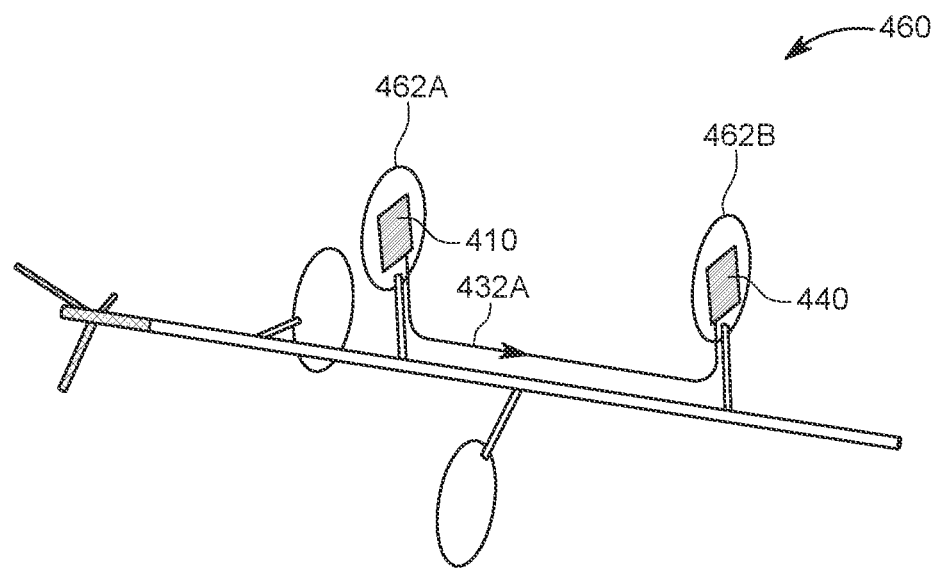
FIGS. 6A to 6G illustrate the distribution of the first and second remote detecting devices over a given plant, by applying a Binary Phase Shift Keying Modulation (BPSK), the gain of the transmitted signal, the encoding scheme used to encode the transmitted signal, the transmitted and received bits, and the theoretical and simulated constellation diagram.
Figure 6B:
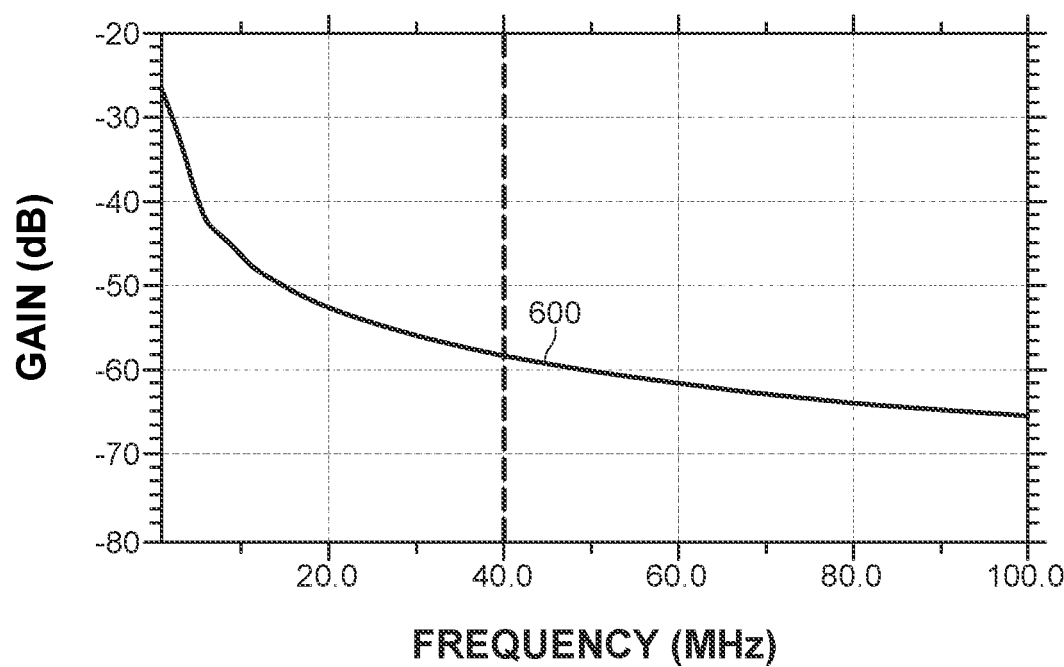
Figure 6C:
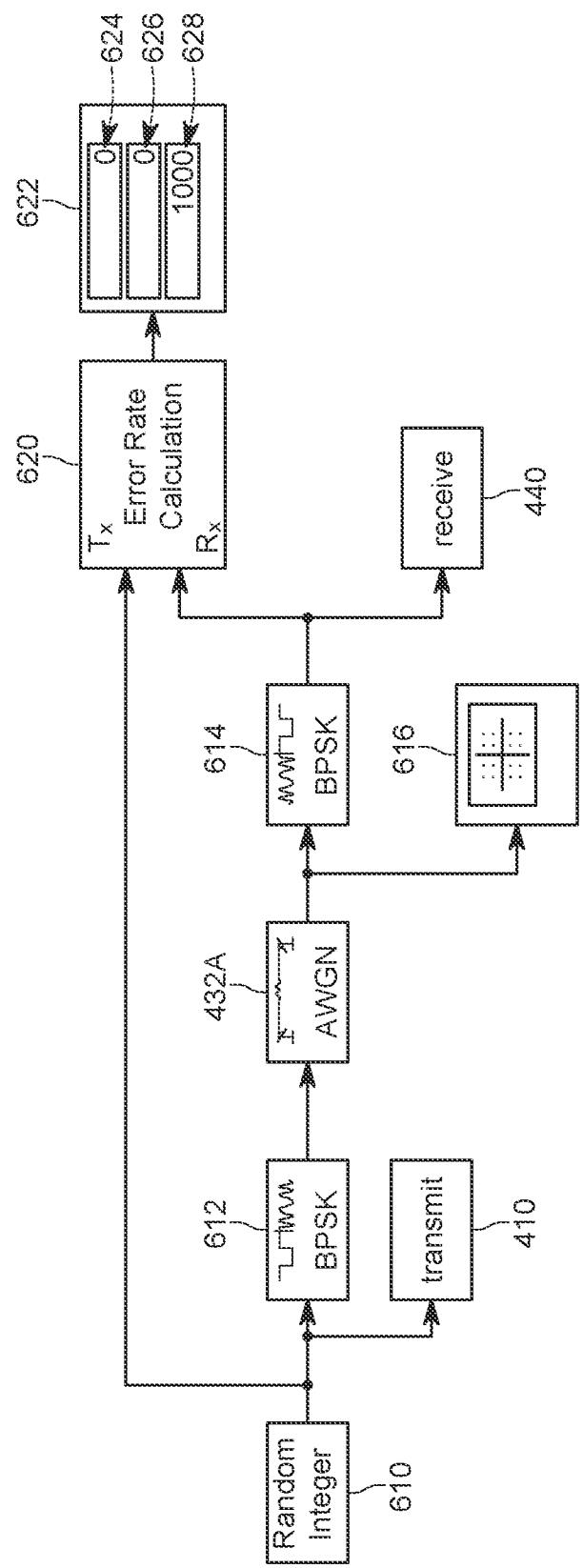

In this respect, FIG. 6A shows a leaf-leaf channel 432A between two leaves 462A and 462B of a given plant 460. An electrode of the transmitter 410 was attached to the first leaf 462A and an electrode of the receiver 440 was attached to the second leaf 462B. By using a simulation tool, for example, Ansoft HFSS, which uses finite analysis for calculating the gain of a given channel, and selecting a main frequency of 40 MHz, the gain 600 of the plant channel 432A is obtained, between the electrodes of the transmitter and receiver, when the frequency is swept between zero and 100 MHz, and the gain is plotted in FIG. 6B. The gain for the main frequency is −58 dB, i.e., 0.00125, which means that the signal is reduced by about 800 times. This signal will be amplified in the receiver to extract the stored information. FIG. 6C shows the Matlab-Simulink model for the channel 432A and includes a random integer generator 610, the transmitter 410, a binary phase shift keying unit 612 for modulating the signal to be transmitted, the plant's body that contributes to the communication channel 432A, a BPSK demodulation unit 614, which is linked to a constellation diagram unit 616, an error rate calculation module 620, and a bit error rate (BER) display 622, having a bit error rate field 624, a number of error bits 626, and a total number of error bits 628. The receiver 440 is linked to the communication channel 432A. In this simulation, it was assumed that the communication channel's Signal-to-Noise (SNR) is 10 dB. For this value, there are 0 bit error per 1000 bits, which results in a 5% BER.

Figure 6D:
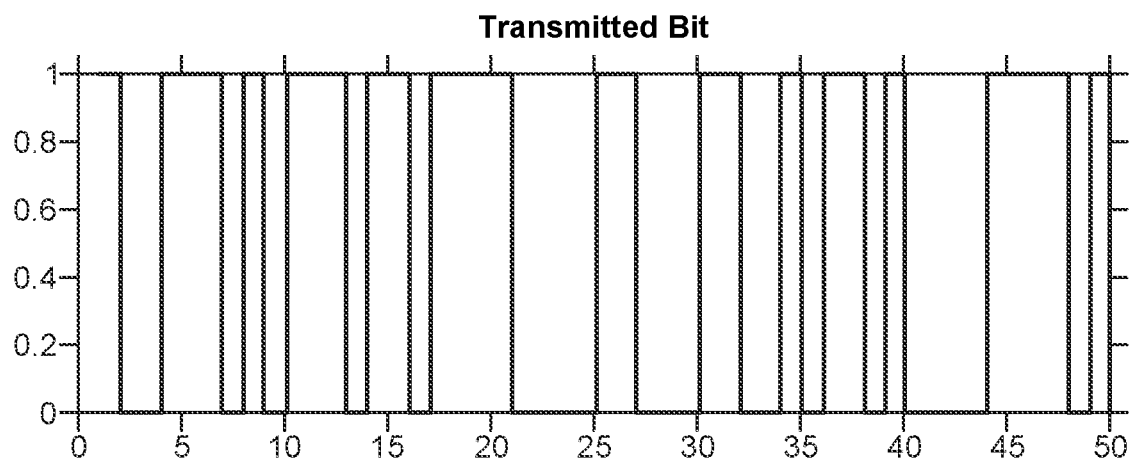
Figure 6E:
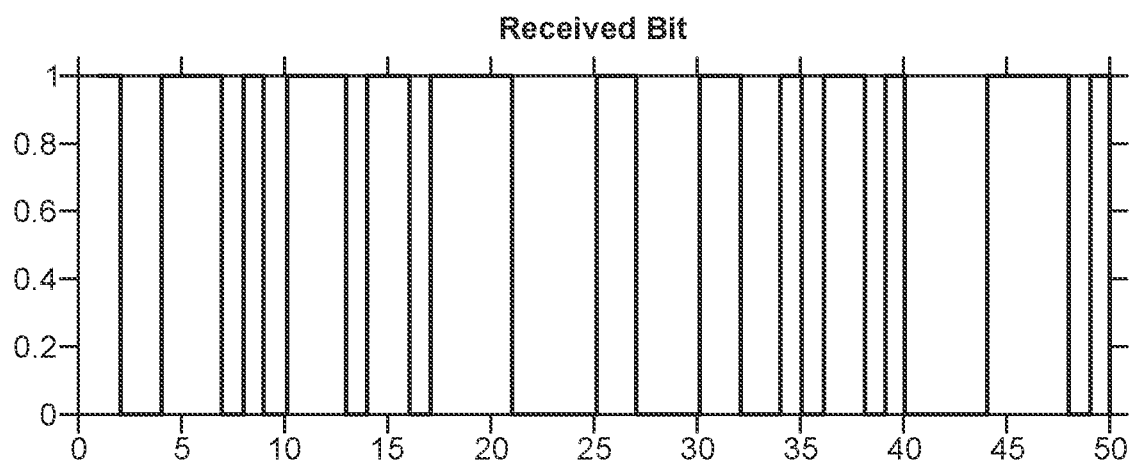
Figure 6F:
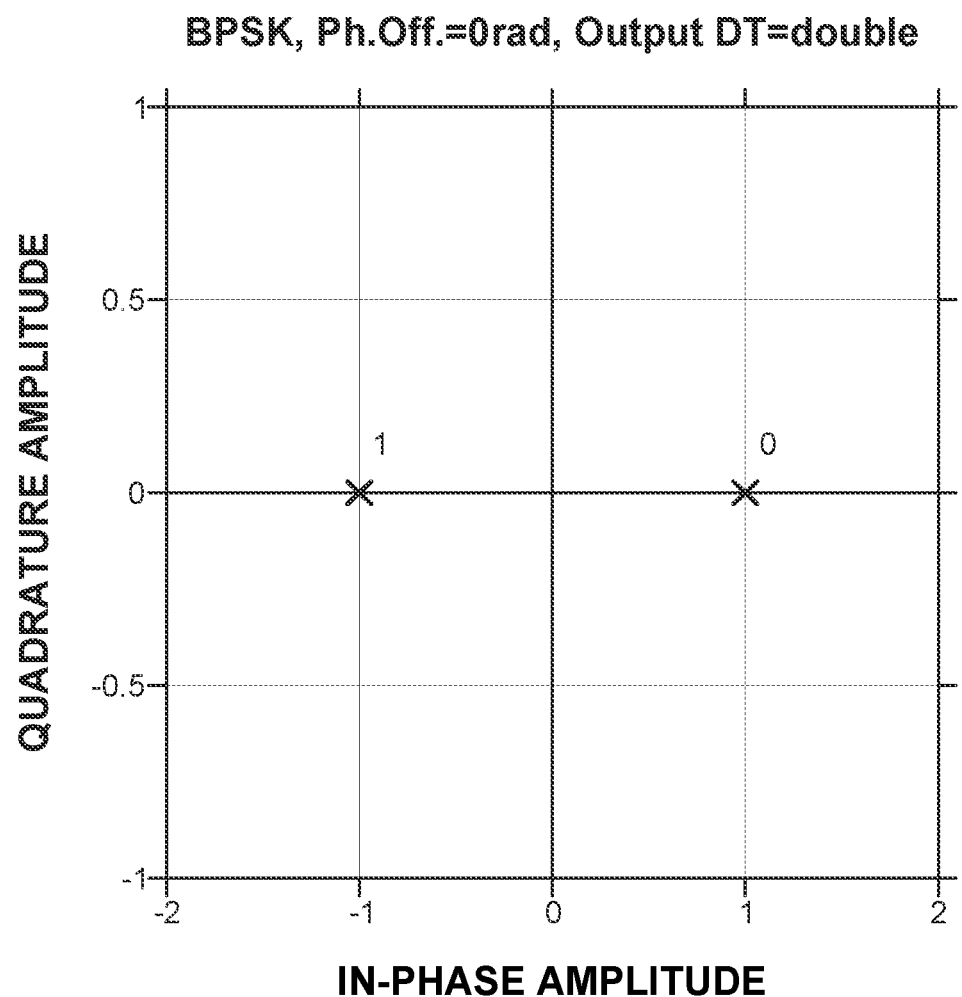
Figure 6G:
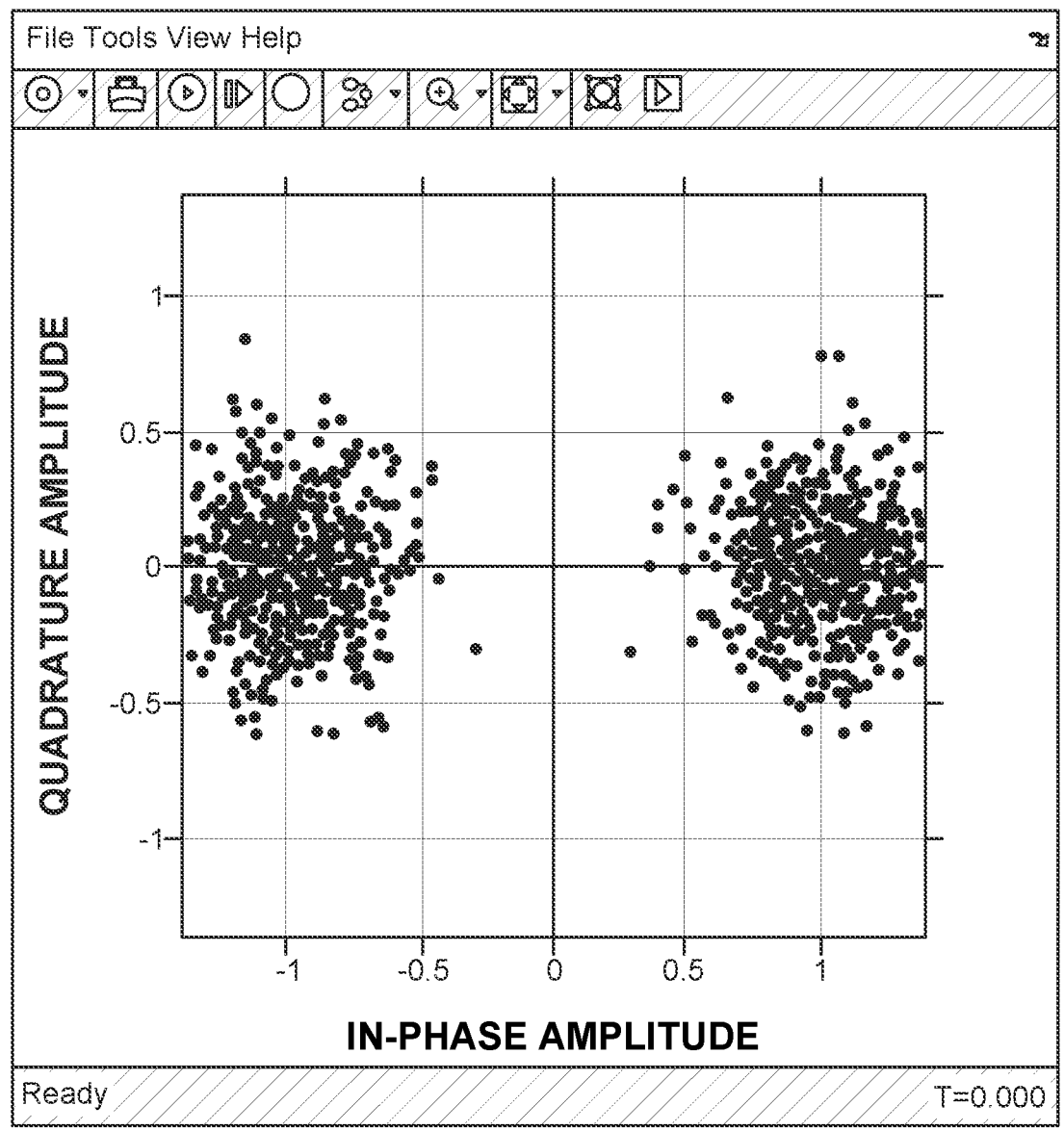

With the BPSK modulation scheme, the signal has two levels, 0 or 1. The bits sent are illustrated in FIG. 6D and the received bits are illustrated in FIG. 6E. An ideal constellation is illustrated in FIG. 6F and has only two points, while the simulated constellation for the plant channel 432A is shown in FIG. 6G, which shows a light spread of the two points.

Figure 7A:
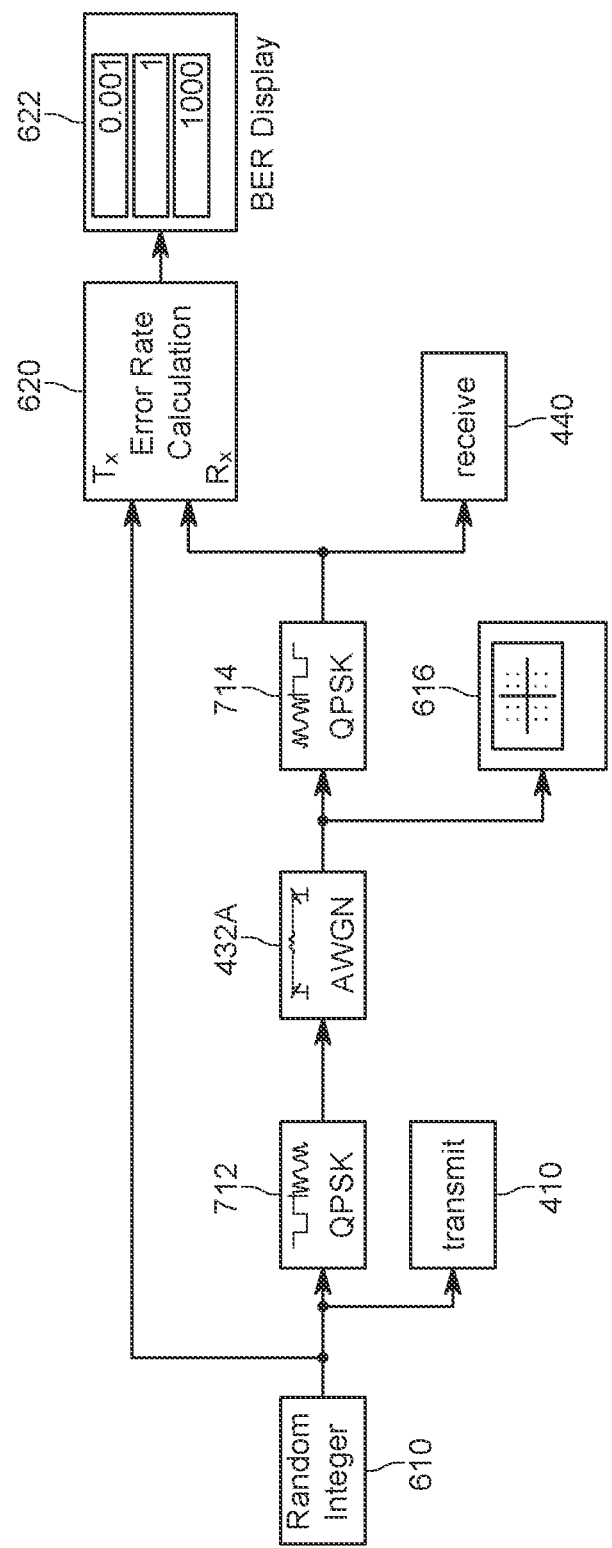
FIG. 7A shows another encoding scheme used for the first and second remote detecting devices when distributed over a given plant, by applying a Quadrature Phase Shift Keying Modulation (QPSK)
Figure 7B:
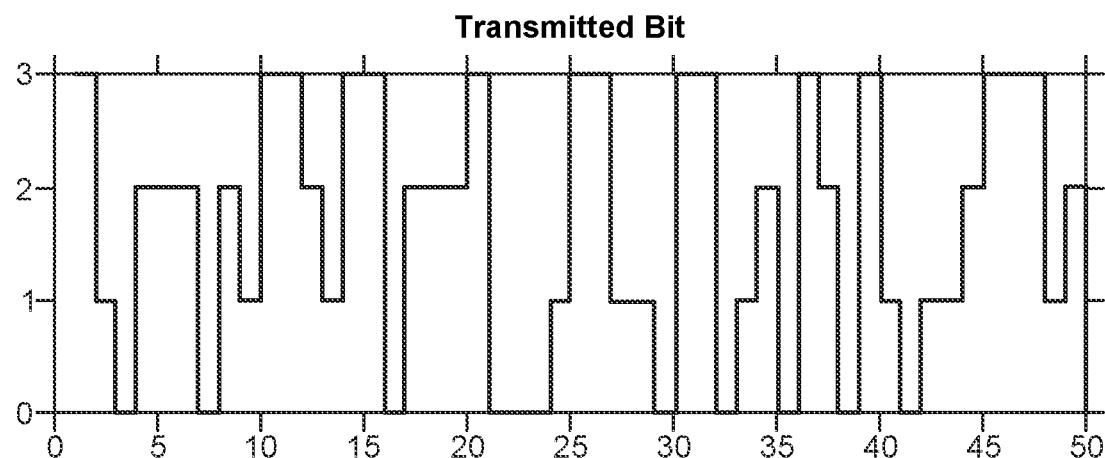
FIGS. 7B to 7E illustrate the transmitted and received bits, and the theoretical and simulated constellation diagram.
Figure 7C:
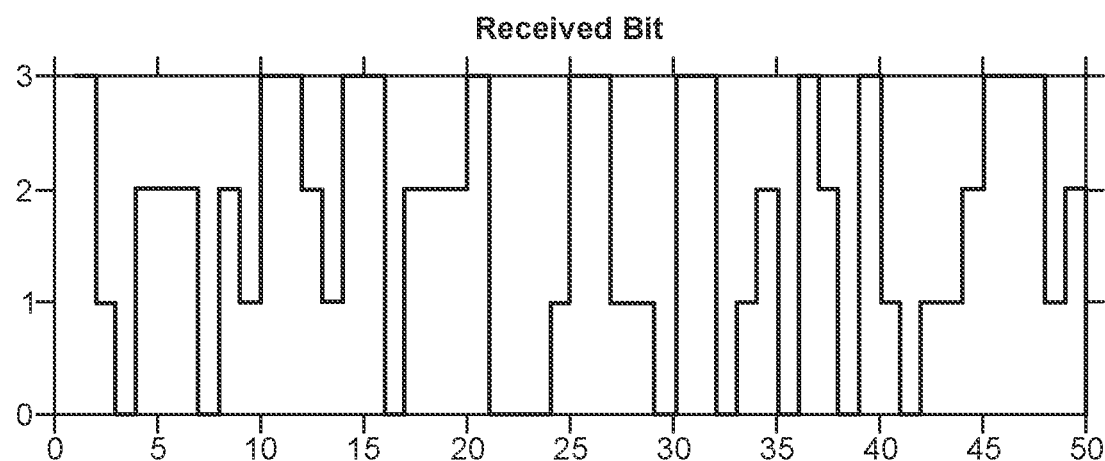
Figure 7D:
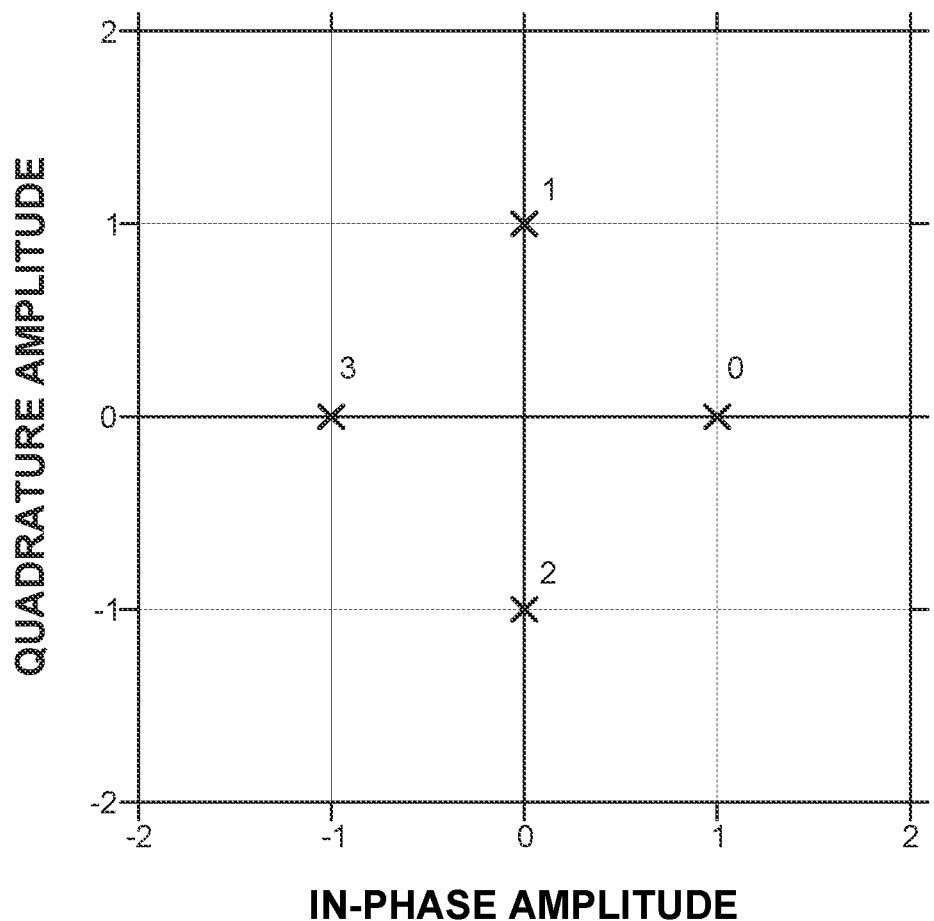
Figure 7E:
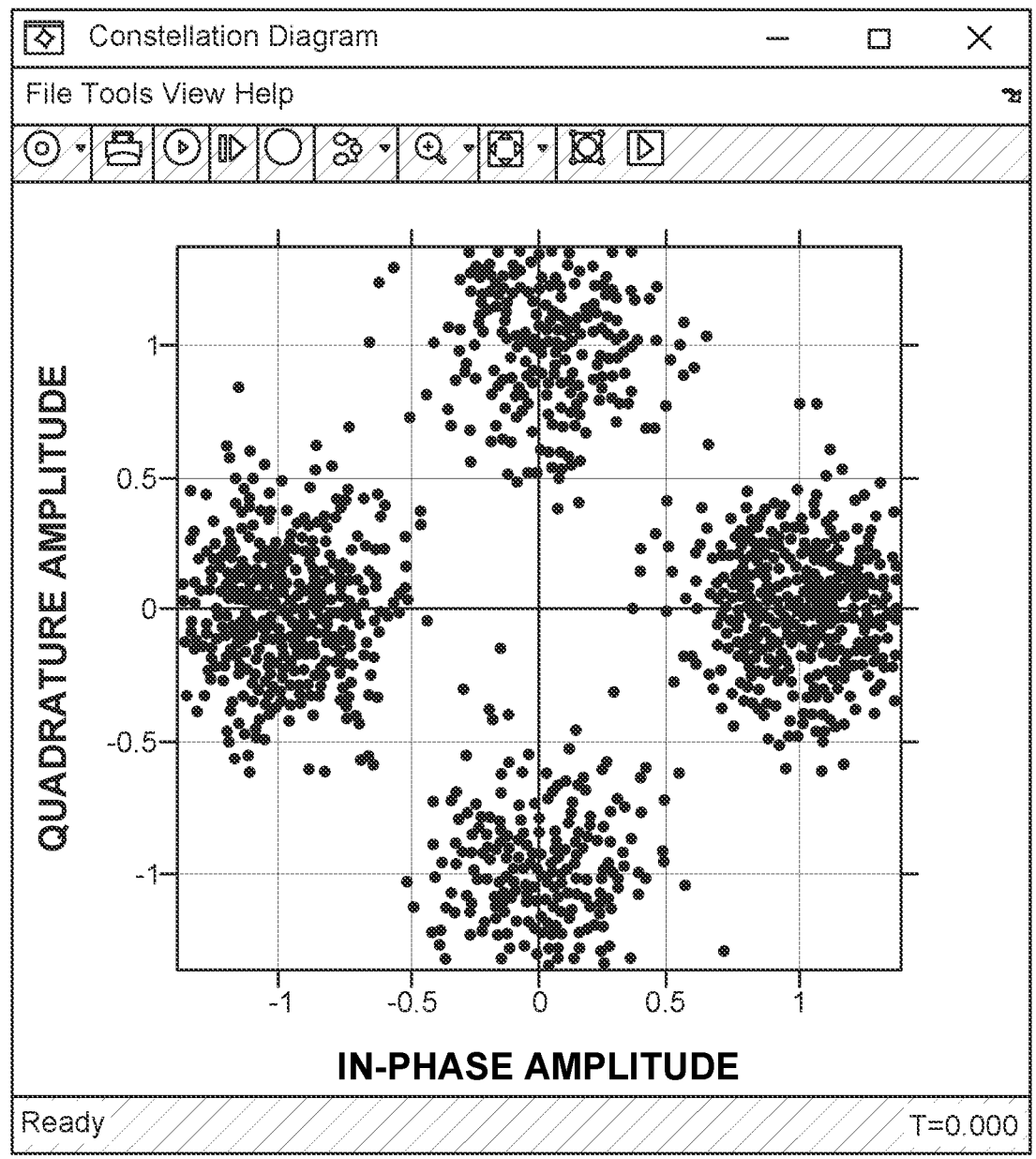

If the quadrature phase shift keying (QPSK) modulation scheme is used for the same plant communication channel 432A, as illustrated in FIG. 7A, the data rate is higher, but the bit error is not zero. FIG. 7A shows the BPSK modules 612 and 614 being replaced by QPSK modules 712 and 714. With the QPSK modulation scheme, the signal has four levels, as shown in FIG. 7B for the transmitted signal and in FIG. 7C for the received signal. The ideal constellation is shown in FIG. 7D and it has four points, while the estimated constellation is shown in FIG. 7E and the points are scattered due to the noise.

Figure 8A:
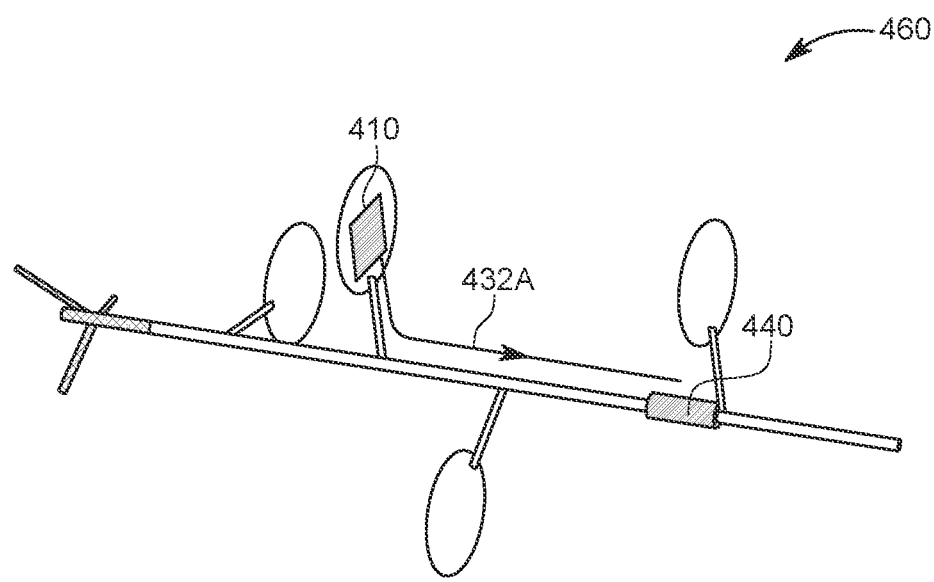
FIGS. 8A and 8B illustrate another distribution of the first and second remote detecting devices over the plant and the corresponding gain curve.
Figure 8B:
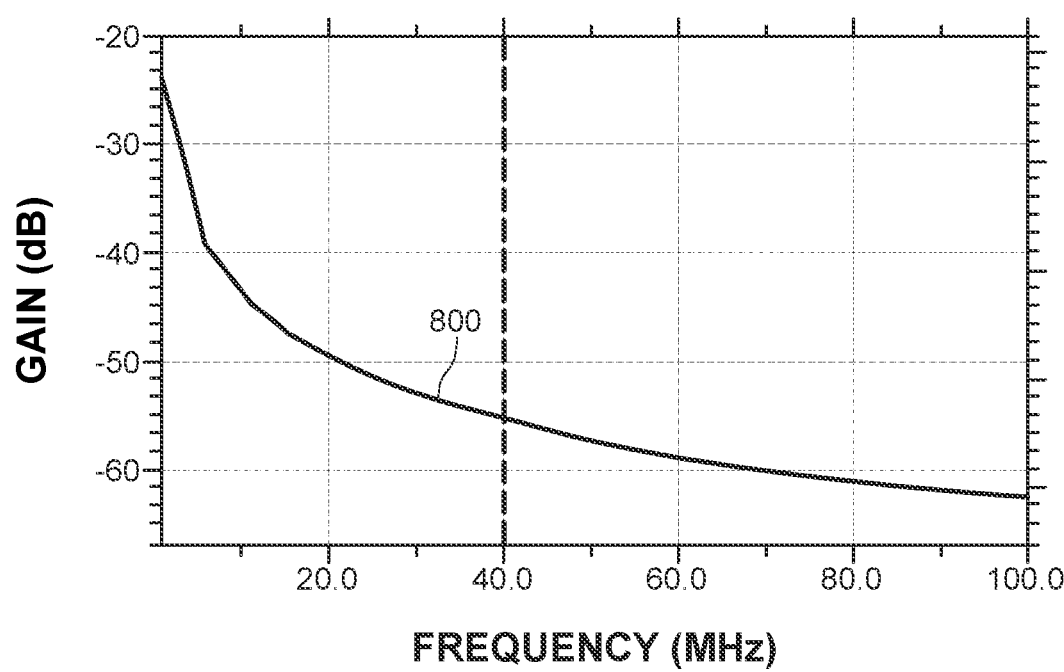
Figure 9A:
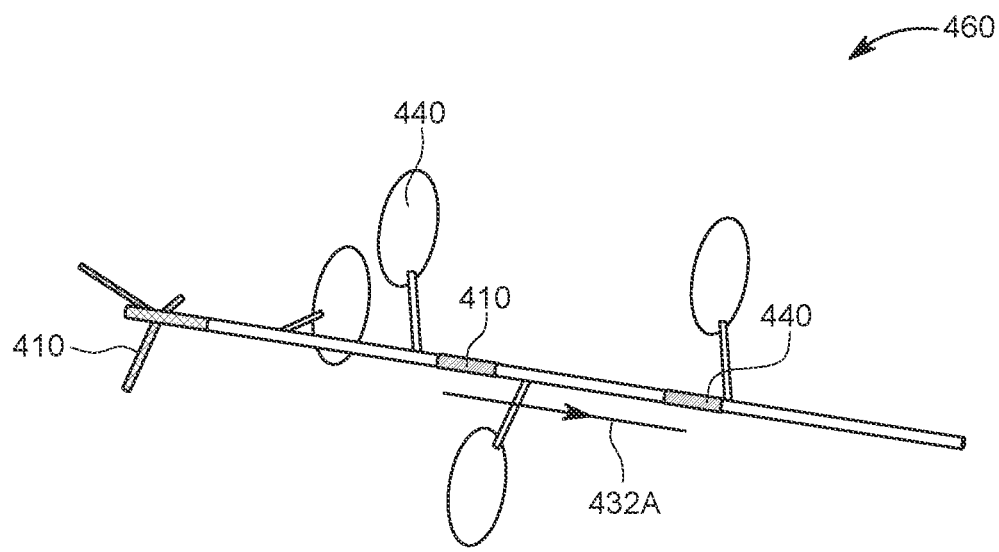
FIGS. 9A and 9B illustrate yet another distribution of the first and second remote detecting devices over the plant and the corresponding gain curve.
Figure 9B:
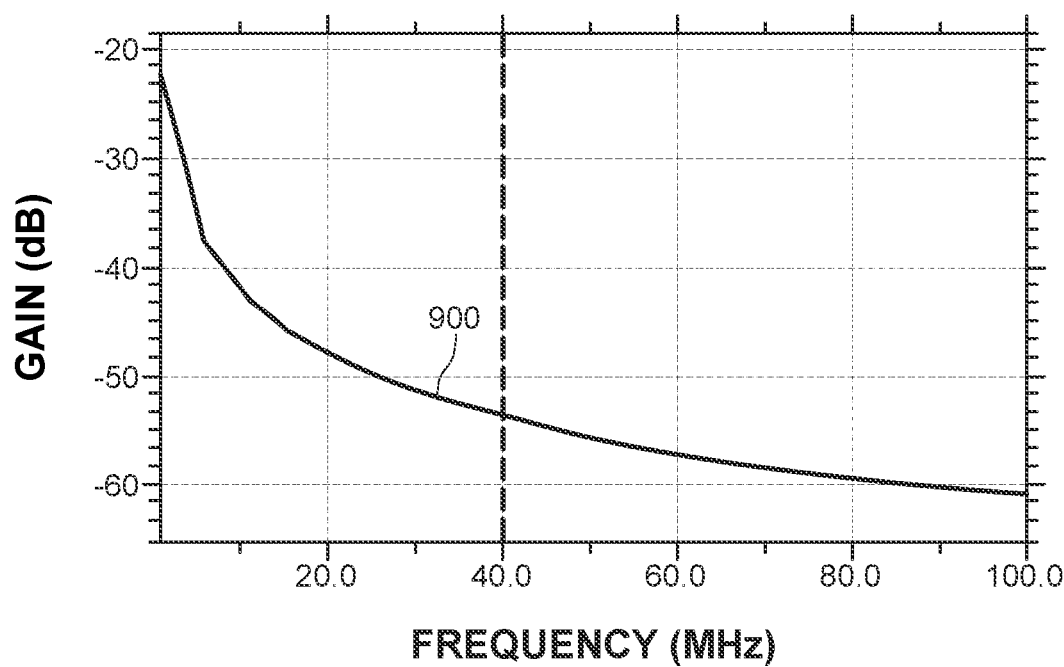

The same simulations were performed for a vent-leaf communication path 432A as illustrated in FIG. 8A, and the gain 800 is illustrated in FIG. 8B. It is noted that for the same main frequency of 40 MHz, the gain is −56 dB, i.e., the signal is reduced by about 633 times. When the QPSK modulation has been applied between the vent and the leaf, the SNR is 12 dB, there is no bit error per 1000 bits, which results in 0% BER. When the same simulations are performed for the vent-vent case, which is illustrated in FIG. 9A, the gain 900 is improved, as shown in FIG. 9B, as the gain is −54 dB, i.e., the signal is reduced by about 500 times.

Figure 10A:
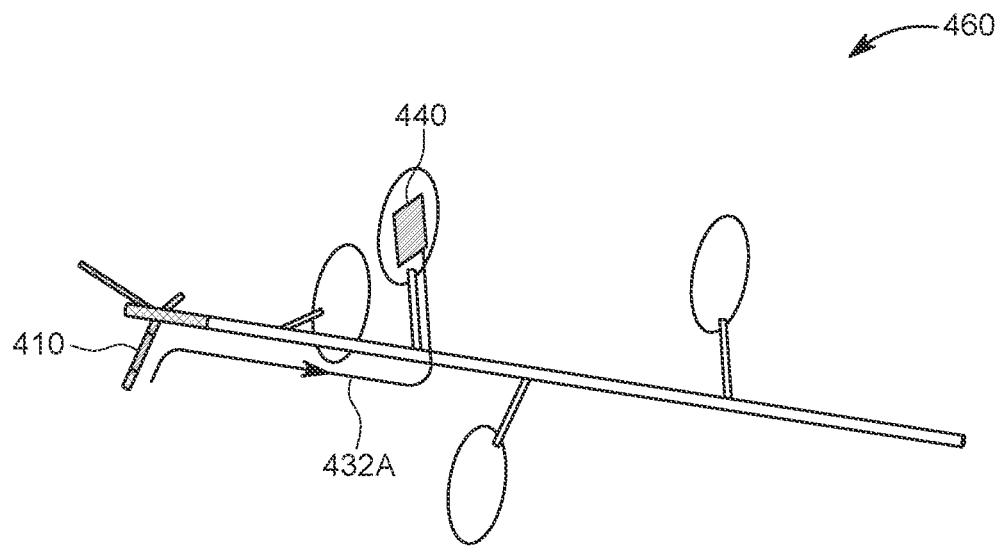
FIGS. 10A and 10B illustrate still another distribution of the first and second remote detecting devices over the plant and the corresponding gain curve.
Figure 10B:
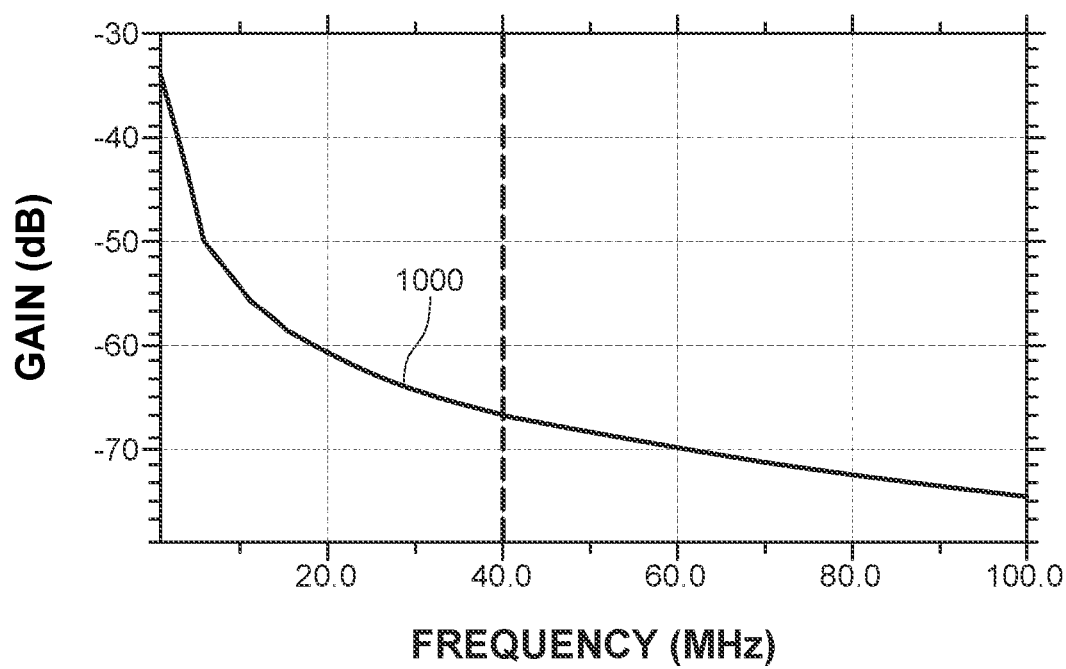

When the same simulations are performed for the root-leaf case, which is illustrated in FIG. 10A, the gain 1000 degrades, as shown in FIG. 10B, as the gain is −66 dB, i.e., the signal is reduced by about 1000 times. For this case, the SNR is 2 dB, and the BER is as high as 18.6%. This case is the worst case scenario because there are two kinds of transition, root to vent and vent to leaf, and the distance between the transmitter and receiver is long.

Figure 11A:
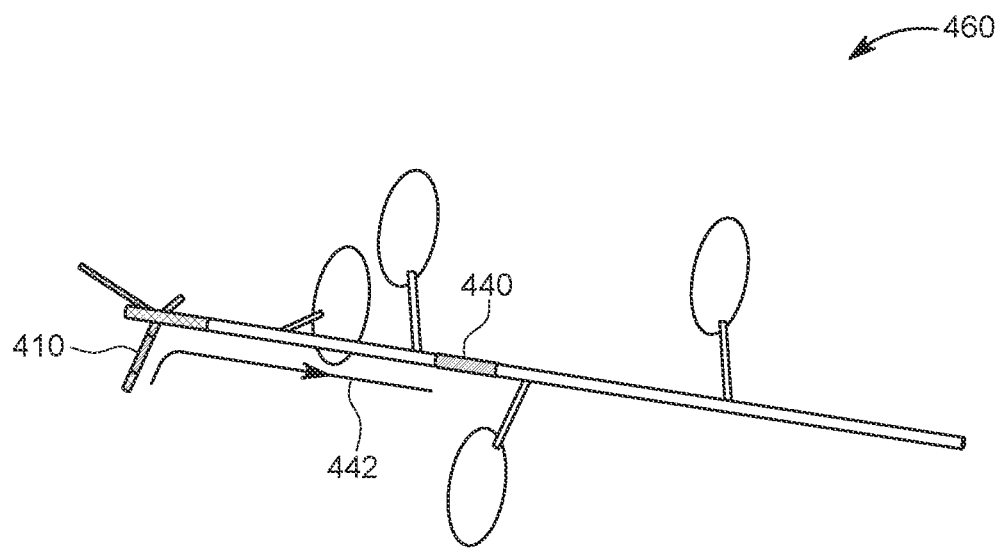
FIGS. 11A and 11B illustrate another distribution of the first and second remote detecting devices over the plant and the corresponding gain curve.
Figure 11B:
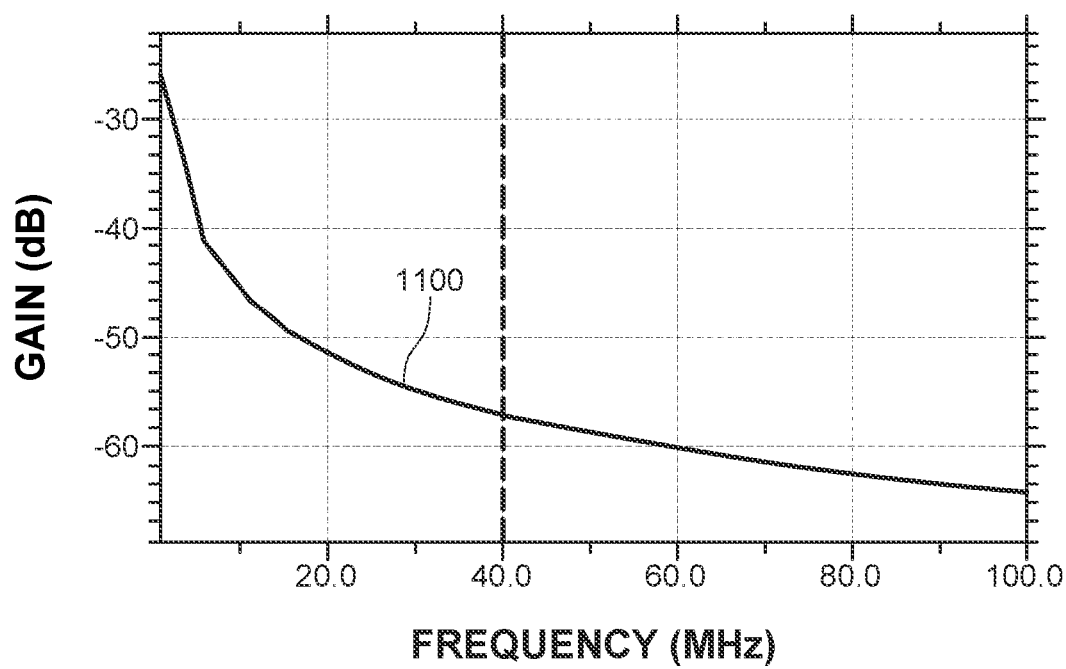
Figure 12A:
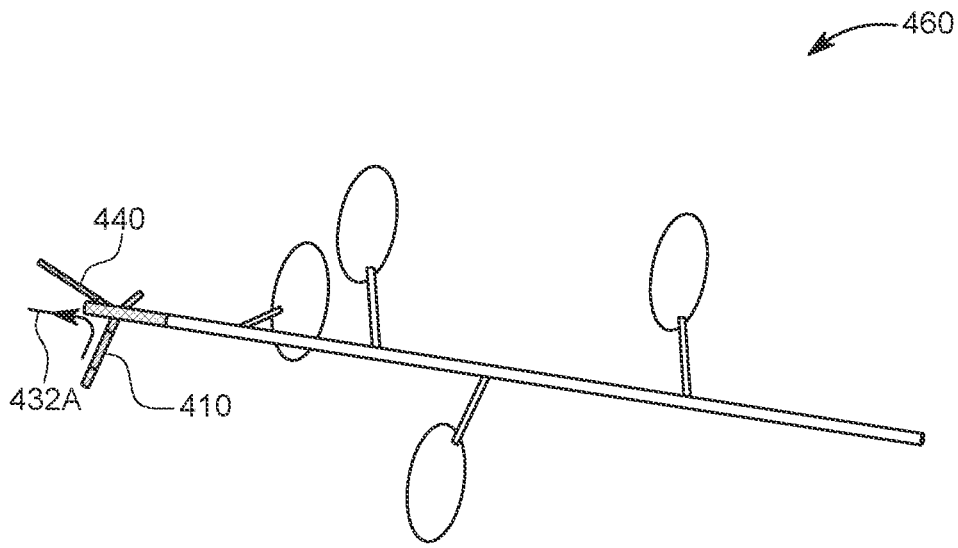
FIGS. 12A and 12B illustrate yet another distribution of the first and second remote detecting devices over the plant and the corresponding gain curve.
Figure 12B:
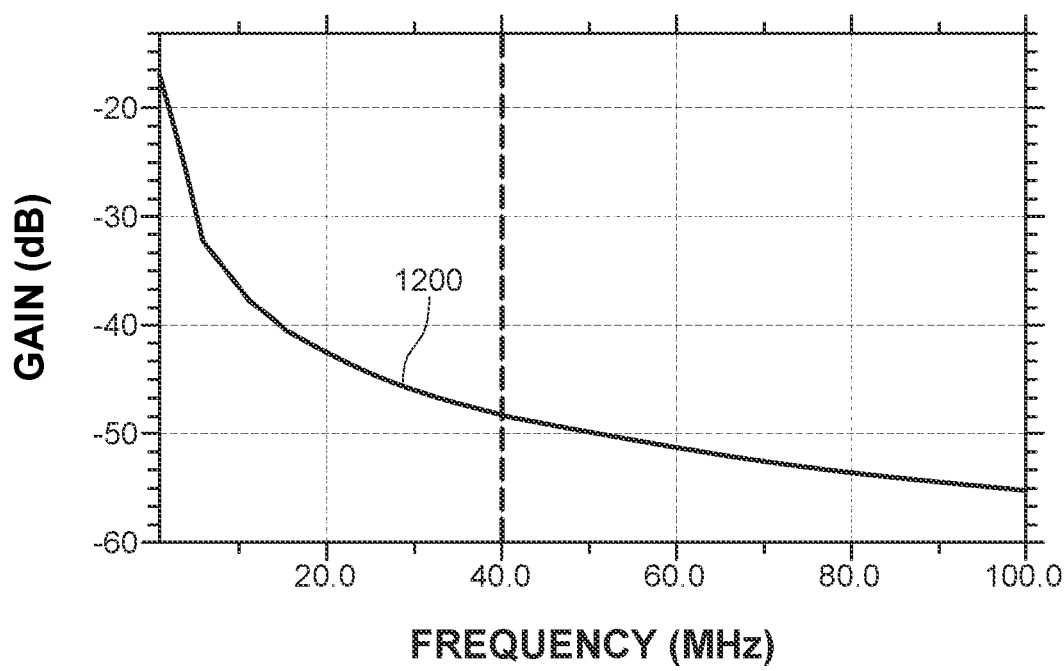

When the same simulations are performed for the root-vent case, which is illustrated in FIG. 11A, the gain 1100 improves, as shown in FIG. 11B, as the gain is −56.5 dB, i.e., the signal is reduced by about 667 times. For this case, the BER is again 0%. For the root-root case, which is illustrated in FIG. 12A, the gain 1200 appears to be the best, at 250, as shown in FIG. 12B, and the BER is 0%. This is the best communication channel because it is the shortest and there are no transitions.

Figure 13:
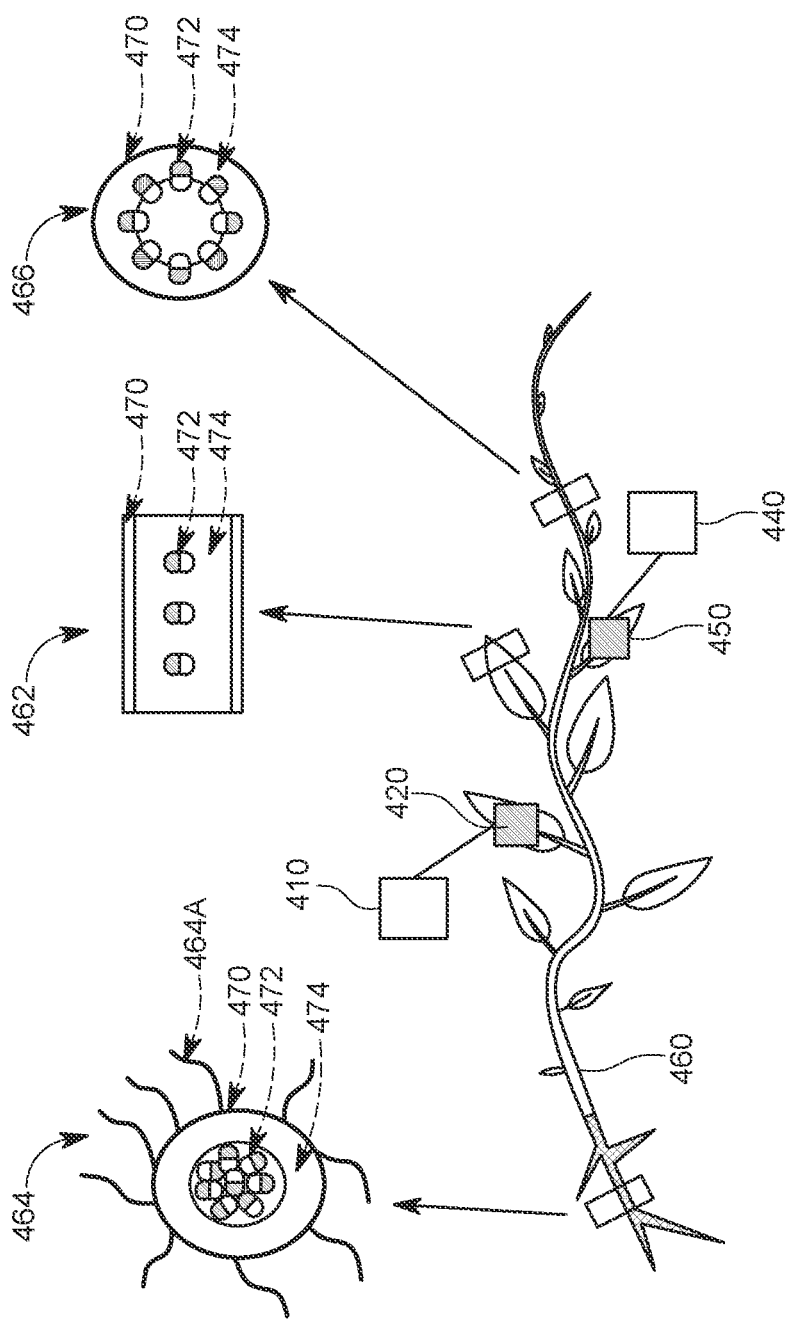
FIG. 13 illustrates various portions of the plant where the first and second remote detecting devices may be placed and the various parts of the plant to which the electrodes of the detecting devices may be attached.

FIG. 13 shows the various parts of a plant 460 that can be used to connect to the electrodes 420, 450 of a receiver 410 or transmitter 440. It is noted that the root tissue 464 has root hair 464A, dermal tissue (epidermal) 470, vascular tissue (xylem, phloem) 472, and ground tissue (cortex) 474. The leaf 462 and the stem 466 also have the dermal tissue (epidermal) 470, vascular tissue (xylem, phloem) 472, and ground tissue (cortex) 474. The electrodes 420, 450 can be connected directly to any of these elements of the plant. In one embodiment, the electrodes are directly connected to the vascular tissue 472.

Those skilled in the art would understand that multiple sensors and corresponding electrodes may be placed along a single plant. For example, if an "X-ray" or "CT scan" of the plant needs to be obtained, than many transmitters are placed over the leaves and stems of the plant, and one or more receivers may be mounted on the roots, to obtain as many as possible plant communication channels. By obtaining the corresponding currents for these plural plant communication channels, for various conditions to which the plant is exposed (for example, too much water, to less water, too much light, too less light, too much food, to little food, to much $CO_2$, to little $CO_2$, and so on), it is possible to map the currents (signals) to the various states of the plant and then, in the control system that coordinates the IoFT, to determine if the plant is in need of anything, or is having too much of something, or is under attack by an insect, etc. In other words, by wiring the plants with the sensors noted above, and by using the plant communication channels, it is possible to "learn" the plant in terms of the measured signals (amplitude, phase, BER, etc.), similar to how a CT scanner or an X-ray machine are used to imagine the human body.

Figure 14:
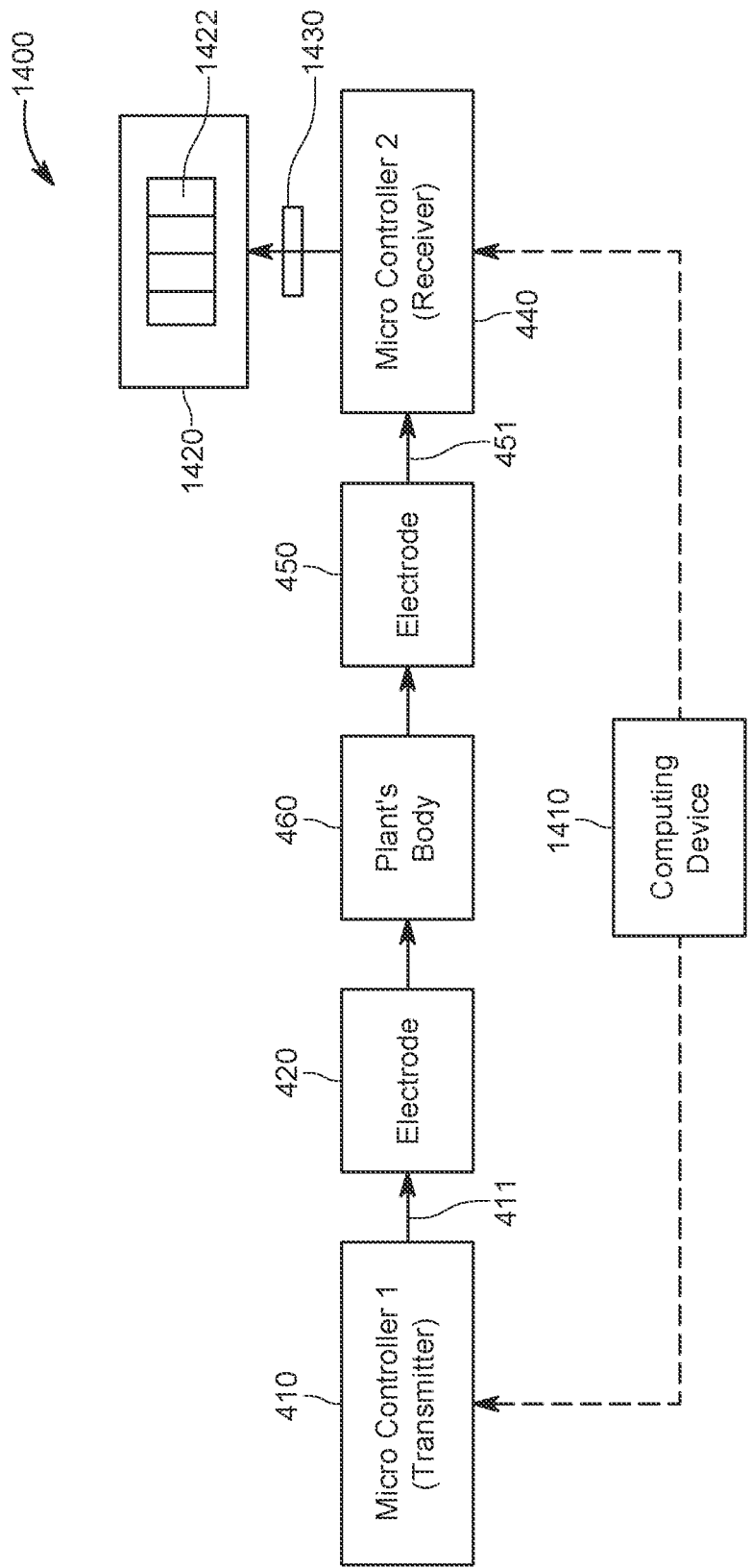
FIG. 14 is a schematic diagram of a system for monitoring a plant by transmitting information along the plant.

Such a system 1400 is schematically illustrated in FIG. 14, and includes the transmitters 410 (only one is shown for simplicity), a given signal 411 that is generated by the transmitter and inputted to the plant through the corresponding electrodes 420, the body of the plant 460, the electrode 450 for the receivers, the receiver 440 (again only one is shown for simplicity), which is configured to detect a signal 451 associated with the given signal 411, a computing device 1410 that may be connected (in a wired or wireless manner) to the transmitter 410 and receiver 440, and a display 1420, for displaying the "image" or a health report 1422 of the plant. The display 1420 may be connected to the control center 330. In the figure, the control center 330, the internet 340, and the sink node 320 are collectively represented as a computing device 1430. The control center 330 may include a processor and associated algorithms for processing the input signals 411 and the associated signals 451, and for generating the health report 1422 of the plant. Note that after the plant 460 is studied under various conditions and with various currents, to learn the plant, the computing device 1410 is removed and the transmitters 410 and receivers 440 operate in an autonomous way, with power being supplied to them either from an internal power source, or from energy collected directly from the plant. Also note that the health report 1422 is generated based on a calibration process, i.e., a healthy plant is monitored with regard to various parameters and the generated currents are recorded, the plant then is exposed to various parameters (heat, water, nutrients, etc.) either in excess or deficit of the normal requirements of the plant, and based on all this data, a status of the plant is mapped on one of many states. Then, when the plant is experiencing various ambient conditions, the measured currents are used to map the status of the plant onto one of the preexisting states of the plant obtained during the calibration process. In another embodiment, a mathematical model may be used to describe the plant, and the measured currents are used as input to the mathematical model. An output of the model is then used to determine the status of the plant.

Thus, having the system 1400, it is possible to translate biological information collected from the plants into electrical/chemical signals capable of generating binary data that can then be used by the user of the control center to determine to what plants are reacting to, in their surroundings. The information collected from the plants may be related to environmental factors affecting crop production (e.g., drastic temperature changes, floods, droughts, pollution), or health-related factors that affect the normal growth of plants (e.g., nutrient deficiencies, invasion of pathogens), and this information may be used by the control center to increase the crop quality and productivity by making use of resources more efficiently (e.g., less pesticides and fertilizers, improved water conservation).

The collected information may also be used to train the plants. The plants may be trained to learn. For example, heliotropic plants learn the optimal direction of the sun and maintain that position of leaf orientation. More complex learning involves reinforcement, and good examples are the plant responses to what are commonly called the stress conditions of cold, drought, heat, heavy metals, soil minerals, salinity, wind sway, flooding, excess/UV light, oxidative stress, herbicides, herbivory, and disease. This learning response enables a quicker, more aggressive, adaptive resistance to subsequent stress episodes. This is clearly a kind of trial-and-error learning (often called Thorndikean learning) and has been called priming in the case of herbivory and disease. Priming is, however, straightforward learning leading to a long-term memory that can last for months. Another term applied only to the abiotic stress stimuli is acclimation, a term that reflects the passive (laboratory) control of plant behavior and ignores the clearly active role played by the wild plant in assessment and response. All the collected information using the system 1400 discussed above may be applied to teaching the plants to respond to the medium in a certain way. In this regard, a fully coupled system of nonlinear, non-autonomous, discontinuous, ordinary differential equations to describe with accuracy the adapting behavior and growth of a single plant may be used as described in the art.

In one embodiment, the system 1400 for collecting information through a plant 460 may include a first remote detecting device 410 attached to a first portion of the plant 460 and configured to transmit a given signal directly through the plant 460, the plant 460, which constitutes a communication channel, a second remote detecting device 440 attached to a second portion of the plant 460, which is different from the first portion, and configured to receive a signal indicative of the transmitted given signal; and a sink node 320 that communicates with the second remote detecting device 440. In one application, the first remote detecting device is a transmitter and the second remote detecting device is a receiver. The transmitter and the receiver may use binary phase shift keying to encode the given signal, or they may use quadrature phase shift keying to encode the given signal. In one embodiment, the first remote detecting device includes a sensor for measuring a parameter associated with the plant, and the given signal is related to the parameter.

Each of the first and second remote detecting devices may include an electrode that is connected to the plant, and the corresponding electrode is placed directly in contact with a vascular tissue of the plant. Further, in one application, each of the first and second remote detecting devices includes an electrode that is connected to the plant, and the corresponding electrode is placed directly in contact with a cortex of the plant. In this application or another application, the first portion is a leaf of the plant and the second portion is a root of the plant. The system may further include additional first remote detecting devices connected to different leaves of the plant. In this or another application, the first remote detecting device communicates with the second remote detecting device exclusively through the first and second portions of the plant.

In another embodiment, the system 1400 may be used for determining a health of the plant 460. The system includes plural transmitters 410 attached to various first portions of the plant 460 and each configured to transmit a given signal 411 directly through the plant 460, the plant 460, which constitutes plural communication channels 432A, 432B, a receiver 440 attached to a second portion of the plant 460, which is different from the first portions, and configured to receive corresponding signals 451 indicative of the transmitted given signals 411, a processing device 1430 that communicates with the second remote detecting device 440 and processes the corresponding signals to generate a health report 1422 of the plant 460, and a display 1420 that displays the health report 1422 of the plant 460.

In this or another embodiment, the transmitters and the receiver use binary phase shift keying to encode the given signal, or a quadrature phase shift keying to encode the given signal. Each of the first transmitters includes a sensor for measuring a parameter associated with the plant, and the given signal is related to the parameter. Each of the transmitters and the receiver includes an electrode that is connected to the plant, and the corresponding electrode is placed directly in contact with a vascular tissue of the plant, or, each of the transmitters and the receiver includes an electrode that is connected to the plant, and the corresponding electrode is placed directly in contact with a cortex of the plant. In this or another application, the first portions are plural leaves of the plant and the second portion is a root of the plant.

Figure 15:
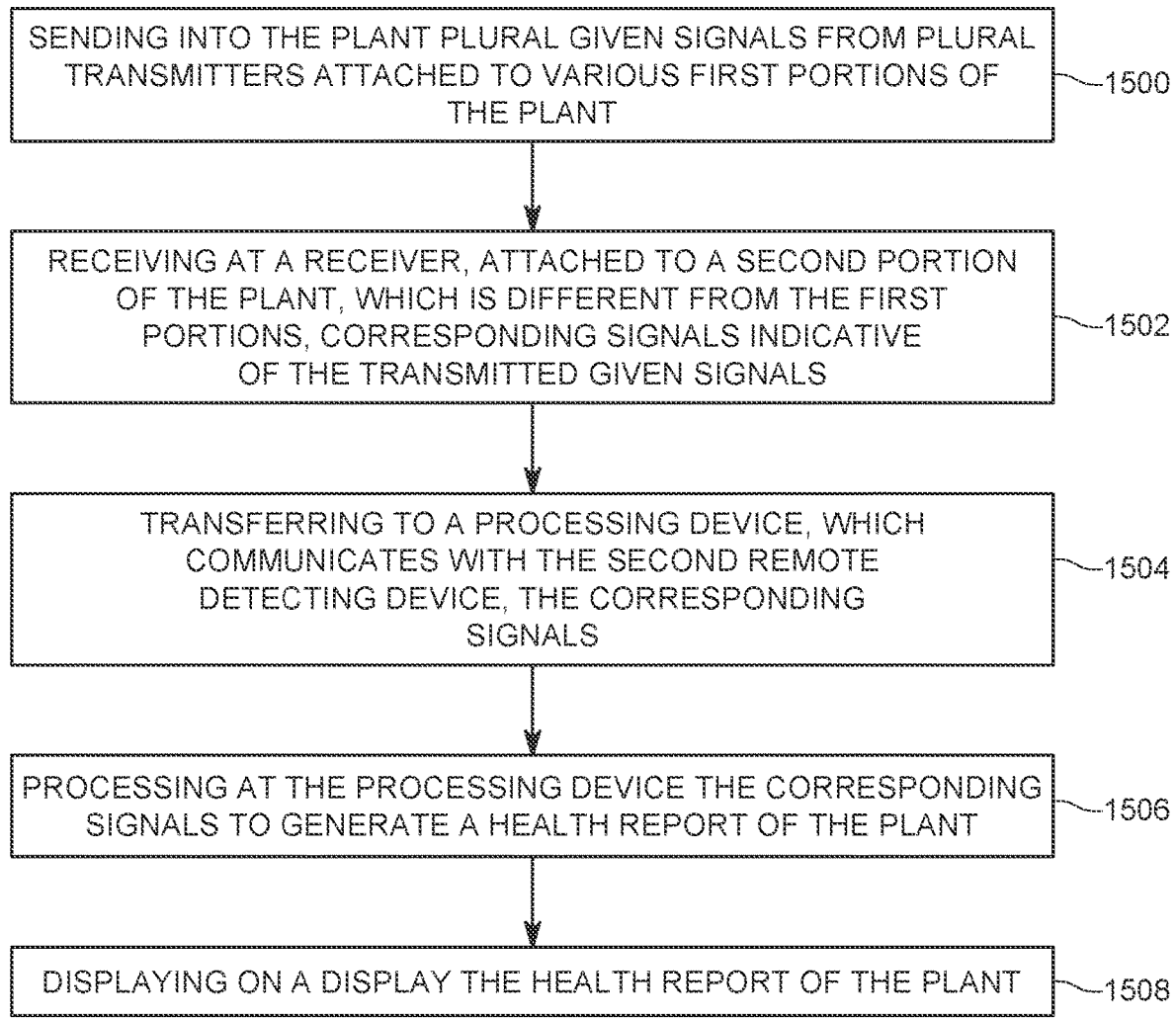
FIG. 15 is a flow chart of a method for monitoring the status of a plant or the status of the ambient of the plant.

A method for determining a health of the plant 460 is now discussed with regard to FIG. 15. The method includes a step 1500 of sending into the plant 460 plural given signals 411 from the plural transmitters 410 attached to various first portions of the plant 460, a step 1502 of receiving at the receiver 440, attached to a second portion of the plant 460, which is different from the first portions, corresponding signals 451 indicative of the transmitted given signals 411, a step 1504 of transferring to the processing device 1430, which communicates with the second remote detecting device 440, the corresponding signals 451, a step 1506 of processing at the processing device 1430 the corresponding signals to generate a health report 1422 of the plant 460, and a step 1508 of displaying on a display 1420 the health report 1422 of the plant 460.

The method may further include a step of encoding the plural given signals before sending them to the plant, and/or a step of attaching an electrode of each of the plural transmitters and the receiver to the plant, and the corresponding electrode is placed directly in contact with a vascular tissue of the plant or with a cortex of the plant, where the first portions are plural leaves of the plant and the second portion is a root of the plant.

The disclosed embodiments provide an Internet of Flora Thing system that is transmitting information through internal channels of one or more plants, where the information is related about the plant or an ambient of the plant. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] Savatin, D. V., Gramegna, G., Modesti, V. and Cervone, F., 2014. Wounding in the plant tissue: the defense of a dangerous passage. Frontiers in plant science, 5, p. 470.
[2] Spoel, S. H. and Dong, X., 2008. Making sense of hormone crosstalk during plant immune responses. Cell host & microbe, 3(6), pp. 348-351.
[3] Lew, T. T. S., Koman, V. B., Gordiichuk, P., Park, M. and Strano, M. S., 2019. The Emergence of Plant Nanobionics and Living Plants as Technology. Advanced Materials Technologies, p. 1900657.

[4] Lee, K., Park, J., Lee, M. S., Kim, J., Hyun, B. G., Kang, D. J., Na, K., Lee, C. Y., Bien, F. and Park, J. U., 2014. In-situ synthesis of carbon nanotube—graphite electronic devices and their integrations onto surfaces of live plants and insects. Nano letters, 14(5), pp. 2647-2654.

[5] Grams, T. E., Lautner, S., Felle, H. H., Matyssek, R. and Fromm, J., 2009. Heat-induced electrical signals affect cytoplasmic and apoplastic pH as well as photosynthesis during propagation through the maize leaf. Plant, Cell & Environment, 32(4), pp. 319-326.

[6] Chatterjee, S. K., Ghosh, S., Das, S., Manzella, V., Vitaletti, A., Masi, E., Santopolo, L., Mancuso, S. and Maharatna, K., 2014. Forward and inverse modelling approaches for prediction of light stimulus from electrophysiological response in plants. Measurement, 53, pp. 101-116.

What is claimed is:

1. A system for collecting information through a plant, the system comprising:
  a first remote detecting device attached to a first portion of the plant and configured to transmit a given signal directly through the plant;
  the plant, which constitutes a communication channel;
  a second remote detecting device attached to a second portion of the plant, which is different from the first portion, and configured to receive a signal indicative of the transmitted given signal; and
  a sink node that communicates with the second remote detecting device.

2. The system of claim 1, wherein the first remote detecting device is a transmitter and the second remote detecting device is a receiver.

3. The system of claim 2, wherein the transmitter and the receiver use binary phase shift keying to encode the given signal.

4. The system of claim 2, wherein the transmitter and the receiver use quadrature phase shift keying to encode the given signal.

5. The system of claim 1, wherein the first remote detecting device includes a sensor for measuring a parameter associated with the plant, and the given signal is related to the parameter.

6. The system of claim 1, wherein each of the first and second remote detecting devices includes an electrode that is connected to the plant, and the corresponding electrode is placed directly in contact with a vascular tissue of the plant.

7. The system of claim 1, wherein each of the first and second remote detecting devices includes an electrode that is connected to the plant, and the corresponding electrode is placed directly in contact with a cortex of the plant.

8. The system of claim 1, wherein the first portion is a leaf of the plant and the second portion is a root of the plant.

9. The system of claim 1, further comprising:
  additional first remote detecting devices connected to different leaves of the plant.

10. The system of claim 1, wherein the first remote detecting device communicates with the second remote detecting device exclusively through the first and second portions of the plant.

11. A system for determining a health of plant, the system comprising:
  plural transmitters attached to various first portions of the plant and each configured to transmit a given signal directly through the plant;
  the plant, which constitutes plural communication channels;
  a receiver attached to a second portion of the plant, which is different from the first portions, and configured to receive corresponding signals indicative of the transmitted given signals;
  a processing device that communicates with the receiver and processes the corresponding signals to generate a health report of the plant; and
  a display that displays the health report of the plant.

12. The system of claim 11, wherein the transmitters and the receiver use binary phase shift keying to encode the given signal.

13. The system of claim 11, wherein the transmitters and the receiver use quadrature phase shift keying to encode the given signal.

14. The system of claim 11, wherein each of the first transmitters includes a sensor for measuring a parameter associated with the plant, and the given signal is related to the parameter.

15. The system of claim 11, wherein each of the transmitters and the receiver includes an electrode that is connected to the plant, and the corresponding electrode is placed directly in contact with a vascular tissue of the plant.

16. The system of claim 11, wherein each of the transmitters and the receiver includes an electrode that is connected to the plant, and the corresponding electrode is placed directly in contact with a cortex of the plant.

17. The system of claim 11, wherein the first portions are plural leaves of the plant and the second portion is a root of the plant.

18. A method for determining a health of a plant, the method comprising:
  sending into the plant plural given signals from plural transmitters attached to various first portions of the plant;
  receiving at a receiver, attached to a second portion of the plant, which is different from the first portions, corresponding signals indicative of the transmitted given signals;
  transferring to a processing device, which communicates with the receiver, the corresponding signals;
  processing at the processing device the corresponding signals to generate a health report of the plant; and
  displaying on a display the health report of the plant.

19. The method of claim 18, further comprising:
  encoding the plural given signals before sending them to the plant.

20. The method of claim 18, further comprising:
  attaching an electrode of each of the plural transmitters and the receiver to the plant, and the corresponding electrode is placed directly in contact with a vascular tissue of the plant or with a cortex of the plant,
  wherein the first portions are plural leaves of the plant and the second portion is a root of the plant.

* * * * *